US010927126B2

(12) United States Patent
Lindsley et al.

(10) Patent No.: US 10,927,126 B2
(45) Date of Patent: Feb. 23, 2021

(54) POSITIVE ALLOSTERIC MODULATORS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); P. Jeffrey Conn, Nashville, TN (US); Darren W. Engers, Brentwood, TN (US); Alison R. Gregro, Mount Juliet, TN (US); Kayla Temple, Spring Hill, TN (US); Paul K. Spearing, Chapel Hill, TN (US); Madeline F. Long, Nashville, TN (US); Julie L. Engers, Brentwood, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 16/347,457

(22) PCT Filed: Nov. 7, 2017

(86) PCT No.: PCT/US2017/060340
§ 371 (c)(1),
(2) Date: May 3, 2019

(87) PCT Pub. No.: WO2018/085813
PCT Pub. Date: May 11, 2018

(65) Prior Publication Data
US 2019/0330231 A1    Oct. 31, 2019

Related U.S. Application Data

(60) Provisional application No. 62/418,668, filed on Nov. 7, 2016, provisional application No. 62/542,626, filed on Aug. 8, 2017.

(51) Int. Cl.
| C07D 495/14 | (2006.01) |
| A61K 31/4375 | (2006.01) |
| A61K 31/5025 | (2006.01) |
| A61K 31/506 | (2006.01) |
| A61K 31/5377 | (2006.01) |
| A61K 45/06 | (2006.01) |
| C07D 519/00 | (2006.01) |

(52) U.S. Cl.
CPC ........ *C07D 495/14* (2013.01); *A61K 31/4375* (2013.01); *A61K 31/506* (2013.01); *A61K 31/5025* (2013.01); *A61K 31/5377* (2013.01); *A61K 45/06* (2013.01); *C07D 519/00* (2013.01)

(58) Field of Classification Search
CPC .................................................. C07D 495/14
USPC ................................................... 514/210.21
See application file for complete search history.

(56) References Cited

U.S. PATENT DOCUMENTS

| 5,594,001 A | 1/1997 | Teleha et al. |
| 5,679,683 A | 10/1997 | Bridges et al. |
| 6,596,726 B1 | 7/2003 | Bridges et al. |
| 7,446,120 B2 | 11/2008 | Gour et al. |
| 8,067,586 B2 | 11/2011 | Hayakawa et al. |
| 8,455,506 B2 | 6/2013 | Qian et al. |
| 8,697,888 B2 | 4/2014 | Lindsley |
| 8,906,922 B2 | 12/2014 | Goff et al. |
| 8,999,988 B2 | 4/2015 | Hurley et al. |
| 9,056,875 B2 | 6/2015 | Lindsley et al. |
| 9,056,876 B2 | 6/2015 | Conn et al. |
| 9,241,916 B2 | 1/2016 | Sinclair et al. |
| 9,353,126 B2 | 5/2016 | Goff et al. |
| 9,981,920 B2 | 5/2018 | Jefson et al. |
| 10,239,887 B2 | 3/2019 | Lindsley et al. |
| 2004/0235809 A1 | 11/2004 | Alexander et al. |
| 2005/0227992 A1 | 10/2005 | Hurley et al. |
| 2008/0160028 A1 | 7/2008 | Reichelt et al. |
| 2009/0029955 A1 | 1/2009 | Pages Santacana et al. |
| 2009/0082336 A1 | 3/2009 | Matasi et al. |
| 2009/0099165 A1 | 4/2009 | Hurley et al. |
| 2009/0105240 A1 | 4/2009 | Mustelin et al. |
| 2009/0105244 A1 | 4/2009 | Rubio Esteban et al. |
| 2010/0009934 A1 | 1/2010 | Rickles et al. |
| 2010/0137585 A1 | 6/2010 | Hayakawa et al. |
| 2010/0298297 A1 | 11/2010 | Zhang et al. |
| 2011/0178107 A1 | 7/2011 | Wang et al. |

(Continued)

FOREIGN PATENT DOCUMENTS

| EP | 1619196 A1 | 1/2006 |
| WO | 2005035537 A2 | 4/2005 |

(Continued)

OTHER PUBLICATIONS

Ansel, Introduction to Pharmaceutical Dosage Forms, 2nd Ed., (1976).

(Continued)

*Primary Examiner* — Kahsay Habte
(74) *Attorney, Agent, or Firm* — Michael Best & Friedrich LLP

(57) ABSTRACT

Disclosed herein are thieno[2,3-b:5,4-c']dipyridin-8-amine and pyrido[4',3':4,5]thieno[2,3-c]pyridazin-8-amine compounds, which may be useful as positive allosteric modulators of the muscarinic acetylcholine receptor $M_4$ (mAChR $M_4$). Also disclosed herein are methods of making the compounds, pharmaceutical compositions comprising the compounds, and methods of treating neurological and psychiatric disorders associated with muscarinic acetylcholine receptor dysfunction using the compounds and compositions.

28 Claims, 1 Drawing Sheet

(56) References Cited

U.S. PATENT DOCUMENTS

| | | | |
|---|---|---|---|
| 2014/0357615 | A1 | 12/2014 | Conn et al. |
| 2014/0364409 | A1 | 12/2014 | Lindsley et al. |
| 2016/0137668 | A1 | 5/2016 | Geneste et al. |
| 2016/0200733 | A1 | 7/2016 | Lindsley et al. |
| 2016/0207935 | A1 | 7/2016 | Lindsley et al. |
| 2017/0369505 | A1 | 12/2017 | Lindsley et al. |

FOREIGN PATENT DOCUMENTS

| | | | |
|---|---|---|---|
| WO | 2005037825 | A2 | 4/2005 |
| WO | 2006010567 | A1 | 2/2006 |
| WO | 2006058723 | A1 | 6/2006 |
| WO | 2006058724 | A1 | 6/2006 |
| WO | 2008011476 | A2 | 1/2008 |
| WO | 2011021038 | A1 | 2/2011 |
| WO | 2012131297 | A1 | 10/2012 |
| WO | 2013096820 | A1 | 6/2013 |
| WO | 2013126856 | A1 | 8/2013 |
| WO | 2014011902 | A1 | 1/2014 |
| WO | 2015027204 | A1 | 2/2015 |
| WO | 2015027214 | A1 | 2/2015 |
| WO | 2017223290 | A1 | 12/2017 |
| WO | 2018085803 | A1 | 5/2018 |
| WO | 2018085808 | A1 | 5/2018 |

OTHER PUBLICATIONS

Aziz et al. 63 Chemical and Pharmaceutical Bulletin, 1015-1028, 2015.
Bodick et al., "Effects of xanomeline, a selective muscarinic receptor agonist, on cognitive function and behavioral symptoms in Alzheimer disease," Arch Neurol. Apr. 1997;54(4):465-73.
Bubser et al., "Selective Activation of M4 Muscarinic Acetylcholine Receptors Reverses MK-801-Induced Behavioral Impairments and Enhances Associative Learning in Rodents," ACS Chem. Neurosci., 2014, 5 (10):920-942.
Bymaster et al., "Potential role of muscarinic receptors in schizophrenia," Life Sci. 1999;64(6-7):527-34.
Bymaster et al., "Unexpected antipsychotic-like activity with the muscarinic receptor ligand (5R,6R)6-(3-propylthio-1,2,5-thiadiazol-4-yl)-1-azabicyclo[3.2.1]octane," Eur J Pharmacol. Sep. 4, 1998;356(2-3):109-19.
C.T.F.A. Cosmetic Ingredient Handbook, 1992, pp. 587-592; Remington's Pharmaceutical Sciences, 15th Ed. 1975, pp. 335-337.
Carruthers, Some Modern Methods of Organic Synthesis, 3rd Edition, Cambridge University Press, Cambridge, 1987.
CAS Abstract and Indexed Compounds Aziz (2015).
CAS Registry Nos. (2011).
Conde-Ceide et al., "Discovery of VU0409551/JNJ-46778212: An mGlu5 Positive Allosteric Modulator Clinical Candidate Targeting Schizophrenia," ACS Med. Chem. Lett., 2015, 6 (6):716-720.
Deeb et al., "Pyridazine and its related compounds. Part 36. Synthesis and antimicrobial activity of some novel pyrimido[40,50:4,5]thieno[2,3-c]pyridazine derivatives," Med Chem Res., 2014, 23:4559-4569.
Furniss et al., "Vogel's Textbook of Practical Organic Chemistry," 5th edition (1989), Longman Scientific & Technical, Essex CM20 2JE, England.
IUPAC 1974 Recommendations for Section E, Fundamental Stereochemistry, in Pure Appl. Chem., 1976, 45: 13-30.
Larock, Comprehensive Organic Transformations, VCH Publishers Inc., New York, 1989.
Liebermann et al., Pharmaceutical Dosage Forms: Tablets (1981).
Loidreau et al., "Synthesis and molecular modelling studies of 8-arylpyrido[3',2':4,5]thieno[3,2-d]pyrimidin-4-amines as multitarget Ser/Thr kinases inhibitors." European journal of medicinal chemistry, 2015; 92:124-34.
McCutcheon's vol. 1, Emulsifiers & Detergents, 1994, North American Edition, pp. 236-239.
Modern Pharmaceutics, Chapters 9 and 10, Banker & Rhodes, eds. (1979).
Morris et al., "Discovery of (S)-2-Cyclopentyl-N-((1-isopropylpyrrolidin2-yl)-9-methyl-1-oxo-2,9-dihydro-1H-pyrrido[3,4-b]indole-4-carboxamide (VU0453379): A Novel, NS Penetrant Glucagon-Like Peptide 1 Receptor (GLP-1R) Positive Allosteric Modulator (PAM)," J. Med. Chem. 2014, 57, 10192-10197.
Periodic Table of Elements, CAS version, Handbook of Chemistry and Physics, 75th edition.
PUBCHEM, "Compound Database, SID 237977984," <https://pubchem.ncbi.nlm.nih.gov/substance/237977984#sectio> Available Date Feb. 13, 2015 (7pages).
Quintela et al., "Synthesis of pyrimido[4',5':4,5]thieno[2,3-c]-pyridazine derivatives," Monatsh Chem., 1996, 127:537-547.
Remington's Pharmaceutical Sciences, 15th Ed. 1975, pp. 335-337.
Shannon et al., "Muscarinic receptor agonists, like dopamine receptor antagonist antipsychotics, inhibit conditioned avoidance response in rats," J Pharmacol Exp Ther. Aug. 1999;290(2):901-7.
Shannon et al., "Xanomeline, an M1/M4 preferring muscarinic cholinergic receptor agonist, produces antipsychotic-like activity in rats and mice," Schizophrenia Res. 2000, 42, 249-259.
Smith and March, March's Advanced Organic Chemistry, 5th Edition, John Wiley & Sons, Inc., New York, 2001.
Sorrell, Organic Chemistry, University Science Books, Sausalito, 1999.
Stanhope et al., "The muscarinic receptor agonist xanomeline has an antipsychotic-like profile in the rat.," J Pharmacol Exp Ther. 2001; 299:782-792.
Wood et al., "Discovery and SAR of a novel series of potent, CNS penetrant M4 PAMs based on a non-enolizable ketone core: Challenges in disposition", Bioorg Med Chem Lett. 2016, vol. 26(17), 4282-4286.
Wuts, PMG, and TW Greene, in Greene's book titled Protective Groups in Organic Synthesis (4th ed.), John Wiley & Sons, NY (2006).
European Patent Extended Search Report for Application No. 17816196.4 dated Nov. 6, 2019 (8 pages).
International Search Report and Written Opinion for Application No. PCT/US2017/038711 dated Nov. 2, 2017, 14 pages.
International Search Report and Written Opinion for Application No. PCT/US2017/060306 dated Jan. 26, 2018, 8 pages.
International Search Report and Written Opinion for Application No. PCT/US2017/060324 dated Jan. 11, 2018, 8 pages.
International Search Report and Written Opinion for Application No. PCT/US2017/060340 dated Feb. 23, 2018, 7 pages.
International Search Report and Written Opinion for Application No. PCT/US2018/064025 dated Feb. 18, 2019, 12 pages.
International Search Report and Written Opinion for Application No. PCT/US2018/064017 dated Feb. 18, 2019, 10 pages.
European Patent Office Extended Search Report for Application No. 17866492.6 dated Apr. 15, 2020 (5 pages).
United States Patent Office Non Final Office Action for U.S. Appl. No. 16/261,108 dated Apr. 13, 2020 (8 pages).
Chilean Patent Office Action for Application No. 3669-2018 dated Dec. 17, 2019 (16 pages including English summary).
European Patent Office Extended Search Report for Application No. 17867920.5 dated Apr. 6, 2020 (8 pages).
Intellectual Propery Office of Singapore Search Report and Written Opinion for Application No. 11201810794V dated Apr. 9, 2020 (8 pages).
Aziz et al., "Discovery of Potent Antiproliferative Agents Targeting EGFR Tyrosine Kinase Based on the Pyrido [3',2':4,5]thieno[3,2-d]pyrimidin-4-amine Scaffold", Chem. Pharm. Bull, vol. 63, 2015, pp. 1015-1028.
European Patent Office Extended Search Report for Application No. 17867018.8 dated Mar. 25, 2020 (6 pages).

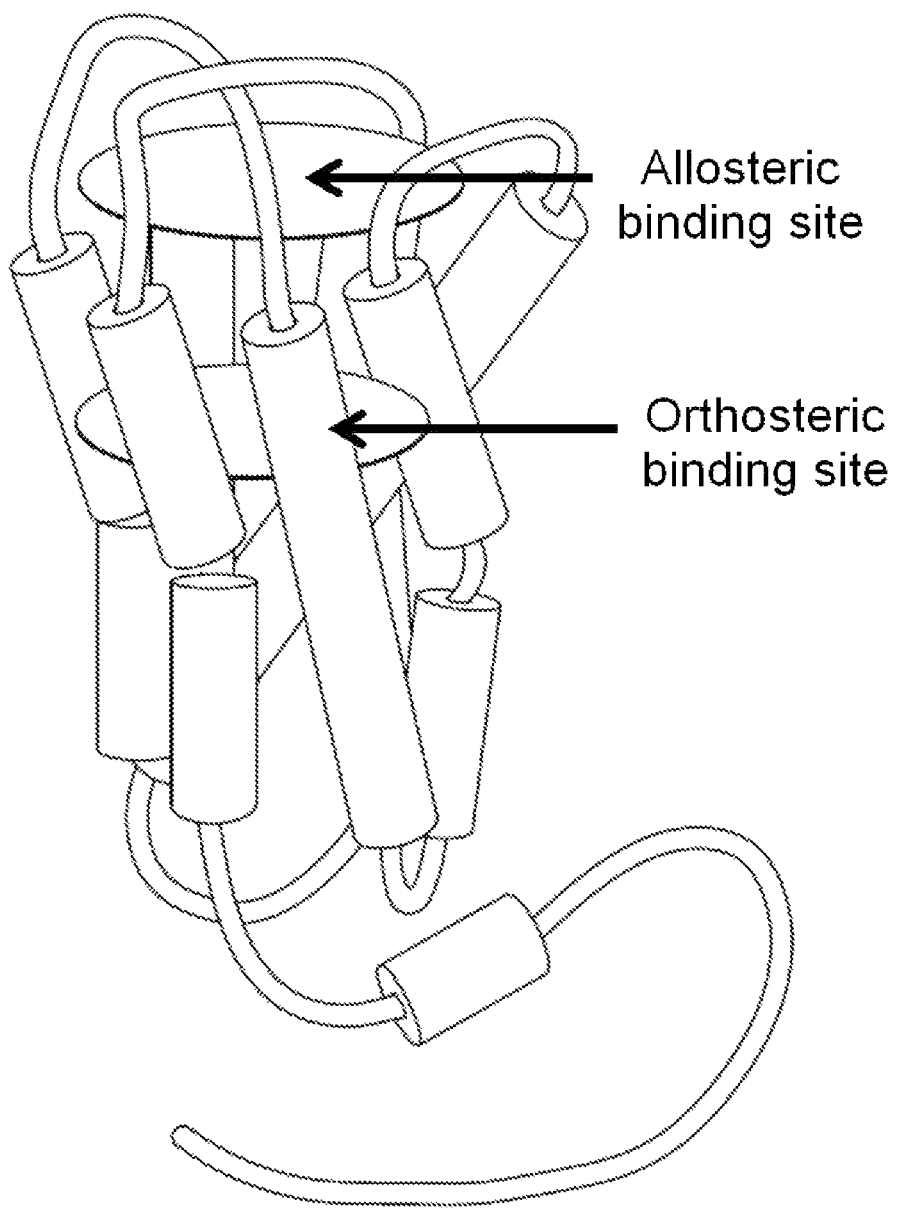

POSITIVE ALLOSTERIC MODULATORS OF THE MUSCARINIC ACETYLCHOLINE RECEPTOR M4

CROSS-REFERENCE TO RELATED APPLICATIONS

This patent application is the U.S. national stage entry, under 35 U.S.C. § 371, of International Application Number PCT/US2017/060340, filed Nov. 7, 2017, which claims the benefit of priority to U.S. Provisional Application No. 62/418,668, filed Nov. 7, 2016, and to U.S. Provisional Application No. 62/542,626, filed Aug. 8, 2017, the entire contents of which are hereby incorporated by reference.

STATEMENT OF GOVERNMENT INTEREST

This invention was made with government support under grant number MH106839 awarded by the National Institutes of Health. The government has certain rights in the invention.

TECHNICAL FIELD

The present disclosure relates to compounds, compositions, and methods for treating neurological and psychiatric disorders associated with muscarinic acetylcholine receptor dysfunction.

BACKGROUND

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, which are critically involved in higher processes. Clinical data supports that cholinergic hypofunction contributes to the cognitive deficits of patients suffering from schizophrenia. Efforts to increase acetylcholine levels have focused on increasing levels of choline, the precursor for acetylcholine synthesis, and on blocking acetylcholinesterase (AChE), the enzyme that metabolizes acetylcholine. As a result, acetylcholinesterase (AChE) inhibitors, which inhibit the hydrolysis of ACh, have been approved in the United States for use in the palliative, but not disease-modifying, treatment of the cognitive deficits in AD patients.

Attempts to augment central cholinergic function through the administration of choline or phosphatidylcholine have not been successful. AChE inhibitors have shown therapeutic efficacy, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility. An alternative approach to pharmacologically target cholinergic hypofunction is the activation of mAChRs, which are widely expressed throughout the body.

The mAChRs are members of the family A G protein-coupled receptors (GPCRs) and include five subtypes, designated $M_1$-$M_5$. The $M_1$, $M_3$ and $M_5$ subtypes mainly couple to $G_q$ and activate phospholipase C, whereas the $M_2$ and $M_4$ subtypes mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. Thus, without wishing to be bound by a particular theory, it is believed that selective agonists of mAChR subtypes that regulate processes involved in cognitive function could prove to be superior therapeutics for treatment of psychosis, schizophrenia and related disorders. The muscarinic $M_4$ receptor has been shown to have a major role in cognitive processing and is believed to have a major role in the pathophysiology of psychotic disorders, including schizophrenia.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_4$ has been viewed as the most likely subtype for mediating the effects of muscarinic acetylcholine receptor dysfunction in psychotic disorders, including schizophrenia, cognition disorders, and neuropathic pain. Because of this, considerable effort has been focused on developing selective $M_4$ agonists for treatment of these disorders. Unfortunately, these efforts have been largely unsuccessful because of an inability to develop compounds that are highly selective for the mAChR $M_4$. Because of this, mAChR agonists that have been tested in clinical studies induce a range of adverse effects by activation of peripheral mAChRs. To fully understand the physiological roles of individual mAChR subtypes and to further explore the therapeutic utility of mAChR ligands in psychosis, including schizophrenia, cognition disorders and other disorders, it can be important to develop compounds that are highly selective activators of mAChR $M_4$ and other individual mAChR subtypes.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly conserved. This approach is proving to be highly successful in developing selective ligands for multiple GPCR subtypes. In the case of mAChRs, a major goal has been to develop allosteric ligands that selectively increase activity of mAChR $M_4$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

More recently, muscarinic agonists including xanomeline have been shown to be active in animal models with similar profiles to known antipsychotic drugs, but without causing catalepsy (Bymaster et al., *Eur. J. Pharmacol.* 1998, 356, 109, Bymaster et al., *Life Sci.* 1999, 64, 527; Shannon et al., *J. Pharmacol. Exp. Ther.* 1999, 290, 901; Shannon et al., *Schizophrenia Res.* 2000, 42, 249). Further, xanomeline was shown to reduce psychotic behavioral symptoms such as delusions, suspiciousness, vocal outbursts, and hallucinations in Alzheimer's disease patients (Bodick et al., *Arch. Neurol.* 1997, 54, 465), however treatment induced side effects, e.g., gastrointestinal effects, have severely limited the clinical utility of this compound.

Despite advances in muscarinic acetylcholine receptor research, there is still a scarcity of compounds that are potent, efficacious, and selective activators of the $M_4$ mAChR and also effective in the treatment of neurological and psychiatric disorders associated with cholinergic activity and diseases in which the muscarinic $M_4$ receptor is involved.

SUMMARY

In one aspect, disclosed are compounds of formula (I),

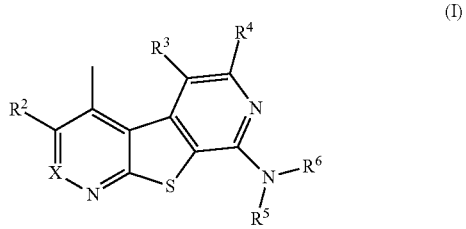

(I)

or a pharmaceutically acceptable salt thereof, wherein:

X is N or $CR^1$;

$R^1$, $R^2$, $R^3$ and $R^4$ are each independently selected from hydrogen, $C_1$-$C_4$-alkyl, $C_1$-$C_4$-haloalkyl, halo, and —$OR^a$;

$R^5$ and $R^6$ are each independently selected from hydrogen, alkyl, alkenyl, alkynyl, aryl, heteroaryl, cycloalkyl, heteroalkyl, heterocycle, and —$(CR^bR^c)_n$—Y, each of which may be optionally substituted;

or $R^5$ and $R^6$ are taken together with the nitrogen atom to which they are attached to form an optionally substituted heterocyclic ring;

Y is selected from halo, —OR, —SR, —C(O)R, —C(O)OR, —S(O)R, —$SO_2$R, —$NR_2$, —C(O)$NR_2$, —S(O)$_2NR_2$, aryl, heteroaryl, cycloalkyl, and heterocycle, each of which may be optionally substituted;

n is 1, 2, 3, 4, 5, 6, 7, or 8;

each $R^a$ is independently selected from hydrogen, $C_1$-$C_4$-alkyl, $C_1$-$C_4$-haloalkyl, aryl, heteroaryl, cycloalkyl, and heterocycle;

$R^b$ and $R^c$ are each independently selected from the group consisting of hydrogen, $C_1$-$C_4$-alkyl, $C_1$-$C_4$-haloalkyl, and halo; and each R is independently selected from the group consisting of hydrogen, alkyl, aryl, arylalkyl, cycloalkyl, cycloalkylalkyl, heterocycle, heterocyclealkyl, heteroaryl, heteroarylalkyl, and heteroalkyl, each of which may be optionally substituted.

Also disclosed are pharmaceutical compositions comprising the compounds, methods of making the compounds, kits comprising the compounds, and methods of using the compounds, compositions and kits for treatment of disorders, such as neurological and/or psychiatric disorders, associated with muscarinic acetylcholine receptor dysfunction in a mammal.

BRIEF DESCRIPTION OF THE DRAWINGS

FIG. 1 shows a schematic illustration of ligand binding sites, including the orthosteric site and an allosteric site, in the muscarinic acetylcholine receptor.

DETAILED DESCRIPTION

Disclosed herein are positive allosteric modulators (i.e. potentiators) of the muscarinic acetylcholine receptor $M_4$ (mAChR $M_4$), methods of making same, pharmaceutical compositions comprising same, and methods of treating neurological and psychiatric disorders associated with muscarinic acetylcholine receptor dysfunction using same. The compounds include thieno[2,3-b:5,4-c']dipyridin-8-amine and pyrido[4',3':4,5]thieno[2,3-c]pyridazin-8-amine compounds.

The human muscarinic acetylcholine receptor $M_4$ (mAChR $M_4$) is a protein of 479 amino acids encoded by the $CHRM_4$ gene. The molecular weight of the unglycosylated protein is about 54 kDa and it is a transmembrane GPCR. As described above, the mAChR $M_4$ is a member of the GPCR Class A family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. A schematic of the structure of mAChR $M_4$ is shown in FIG. 1, with the transmembrane segments shown as cylindrical shapes (which span the lipid bilayer of the cell membrane). The orthosteric binding for natural ligand, acetylcholine, for mAChRs is within a pocket located in the transmembrane segments as depicted in FIG. 1.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved. Without wishing to be bound by a particular theory, the disclosed compounds and products of the disclosed methods are believed to bind to an allosteric site distinct from the orthosteric binding site. For example, a disclosed compound can bind at the binding site as illustrated in FIG. 1.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; *Carruthers, Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, and tetrahydroquinolinyl.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, cycloheptenyl, and bicyclo[2.2.1]heptenyl (e.g., bicyclo[2.2.1]hept-5-en-2-yl).

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "═══" designates a single bond (——) or a double bond (══).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

The term "orthosteric site" as used herein refers to the primary binding site on a receptor that is recognized by the endogenous ligand or agonist for that receptor. For example, the orthosteric site in the mAChR M$_4$ receptor is the site that acetylcholine binds.

The term "mAChR M$_4$ receptor positive allosteric modulator" as used herein refers to any exogenously administered compound or agent that directly or indirectly augments the activity of the mAChR M$_4$ receptor in the presence or in the absence of acetylcholine, or another agonist, in an animal, in particular a mammal, for example a human. For example, a mAChR M$_4$ receptor positive allosteric modulator can increase the activity of the mAChR M$_4$ receptor in a cell in the presence of extracellular acetylcholine. The cell can be Chinese hamster ovary (CHO-K1) cells transfected with human mAChR M$_4$. The cell can be Chinese hamster ovary (CHO-K1) cells transfected with rat mAChR M$_4$ receptor. The cell can be Chinese hamster ovary (CHO-K1) cells transfected with a mammalian mAChR M$_4$. The term "mAChR M$_4$ receptor positive allosteric modulator" includes a compound that is a "mAChR M$_4$ receptor allosteric potentiator" or a "mAChR M$_4$ receptor allosteric agonist," as well as a compound that has mixed activity comprising pharmacology of both an "mAChR M$_4$ receptor allosteric potentiator" and an "mAChR M$_4$ receptor allosteric agonist." The term "mAChR M$_4$ receptor positive allosteric modulator also includes a compound that is a "mAChR M$_4$ receptor allosteric enhancer."

The term "mAChR M$_4$ receptor allosteric potentiator" as used herein refers to any exogenously administered compound or agent that directly or indirectly augments the response produced by the endogenous ligand (such as acetylcholine) when the endogenous ligand binds to the orthosteric site of the mAChR M$_4$ receptor in an animal, in particular a mammal, for example a human. The mAChR M$_4$ receptor allosteric potentiator binds to a site other than the orthosteric site, that is, an allosteric site, and positively augments the response of the receptor to an agonist or the endogenous ligand. In some embodiments, an allosteric potentiator does not induce desensitization of the receptor, activity of a compound as an mAChR M$_4$ receptor allosteric potentiator provides advantages over the use of a pure mAChR M$_4$ receptor orthosteric agonist. Such advantages can include, for example, increased safety margin, higher tolerability, diminished potential for abuse, and reduced toxicity.

The term "mAChR M$_4$ receptor allosteric enhancer" as used herein refers to any exogenously administered compound or agent that directly or indirectly augments the response produced by the endogenous ligand (such as acetylcholine) in an animal, in particular a mammal, for example a human. In some embodiments, the allosteric enhancer increases the affinity of the natural ligand or agonist for the orthosteric site. In some embodiments, an allosteric enhancer increases the agonist efficacy. The mAChR M$_4$ receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

The term "mAChR M$_4$ receptor allosteric agonist" as used herein refers to any exogenously administered compound or agent that directly activates the activity of the mAChR M$_4$ receptor in the absence of the endogenous ligand (such as acetylcholine) in an animal, in particular a mammal, for example a human. The mAChR M$_4$ receptor allosteric agonist binds to a site that is distinct from the orthosteric acetylcholine site of the mAChR M$_4$ receptor. Because it does not require the presence of the endogenous ligand, activity of a compound as an mAChR M$_4$ receptor allosteric agonist provides advantages if cholinergic tone at a given synapse is low.

The term "mAChR M$_4$ receptor neutral allosteric ligand" as used herein refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed is a compound of formula (I):

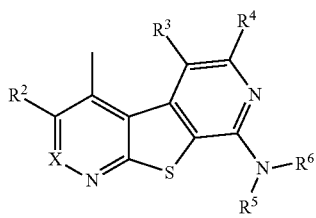

(I)

or a pharmaceutically acceptable salt thereof, wherein:

X is N or $CR^1$;

$R^1$, $R^2$, $R^3$ and $R^4$ are each independently selected from hydrogen, $C_1$-$C_4$-alkyl, $C_1$-$C_4$-haloalkyl, halo, and —$OR^a$;

$R^5$ and $R^6$ are each independently selected from hydrogen, alkyl, alkenyl, alkynyl, aryl, heteroaryl, cycloalkyl, heteroalkyl, heterocycle, and —$(CR^bR^c)_n$—Y, each of which may be optionally substituted;

or $R^5$ and $R^6$ are taken together with the nitrogen atom to which they are attached to form an optionally substituted heterocyclic ring;

Y is selected from halo, —OR, —SR, —C(O)R, —C(O)OR, —S(O)R, —$SO_2$R, —$NR_2$, —C(O)$NR_2$, —S(O)$_2NR_2$, aryl, heteroaryl, cycloalkyl, and heterocycle, each of which may be optionally substituted;

n is 1, 2, 3, 4, 5, 6, 7, or 8;

each $R^a$ is independently selected from hydrogen, $C_1$-$C_4$-alkyl, $C_1$-$C_4$-haloalkyl, aryl, heteroaryl, cycloalkyl, and heterocycle;

$R^b$ and $R^c$ are each independently selected from the group consisting of hydrogen, $C_1$-$C_4$-alkyl, $C_1$-$C_4$-haloalkyl, and halo; and each R is independently selected from the group consisting of hydrogen, alkyl, aryl, arylalkyl, cycloalkyl, cycloalkylalkyl, heterocycle, heterocyclealkyl, heteroaryl, heteroarylalkyl, and heteroalkyl, each of which may be optionally substituted.

In some embodiments, X is N. In some embodiments, X is $CR^1$. In some embodiments, $R^1$ is $C_1$-$C_4$ alkyl. In some embodiments, $R^1$ is methyl.

In some embodiments, $R^2$ is hydrogen. In some embodiments, $R^2$ is $C_1$-$C_4$ alkyl. In some embodiments, $R^2$ is methyl. In some embodiments, $R^2$ is halo. In some embodiments, $R^2$ is chloro. In some embodiments, $R^2$ is $C_1$-$C_4$-haloalkyl. In some embodiments, $R^2$ is difluoromethyl. In some embodiments, $R^2$ is —$OR^a$, wherein $R^a$ is $C_1$-$C_4$ alkyl. In some embodiments, $R^2$ is methoxy.

In some embodiments, X is $CR^1$, $R^1$ is $C_1$-$C_4$ alkyl, and $R^2$ is selected from hydrogen and halo. In some embodiments, X is $CR^1$, $R^1$ is $C_1$-$C_4$ alkyl, and $R^2$ is selected from hydrogen and chloro. In some embodiments, X is $CR^1$, $R^1$ is $C_1$-$C_4$ alkyl, and $R^2$ is hydrogen. In some embodiments, X is $CR^1$, $R^1$ is methyl, and $R^2$ is hydrogen. In some embodiments, X is $CR^1$, $R^1$ is $C_1$-$C_4$ alkyl, and $R^2$ is halo. In some embodiments, X is $CR^1$, $R^1$ is methyl, and $R^2$ is chloro.

In some embodiments, X is N, and $R^2$ is selected from $C_1$-$C_4$-alkyl, $C_1$-$C_4$-haloalkyl, halo, and —$OR^a$, wherein $R^a$ is $C_1$-$C_4$-alkyl. In some embodiments, X is N, and $R^2$ is selected from methyl, difluoromethyl, chloro, and methoxy. In some embodiments, X is N, and $R^2$ is $C_1$-$C_4$-alkyl. In some embodiments, X is N, and $R^2$ is methyl. In some embodiments, X is N, and $R^2$ is $C_1$-$C_4$-haloalkyl. In some embodiments, X is N, and $R^2$ is difluoromethyl. In some embodiments, X is N, and $R^2$ is halo. In some embodiments, X is N, and $R^2$ is chloro. In some embodiments, X is N, and $R^2$ is —$OR^a$, wherein $R^a$ is $C_1$-$C_4$-alkyl. In some embodiments, X is N, and $R^2$ is methoxy.

In some embodiments, $R^3$ is hydrogen. In some embodiments, $R^3$ is halo. In some embodiments, $R^3$ is chloro.

In some embodiments, $R^4$ is hydrogen.

In some embodiments, the compound is a compound of formula (Ia):

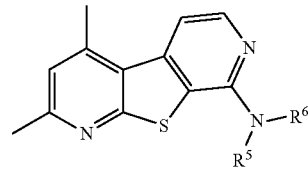

(Ia)

or a pharmaceutically acceptable salt thereof, wherein $R^5$ and $R^6$ are as defined in the embodiments described herein.

In some embodiments, the compound is a compound of formula (Ib):

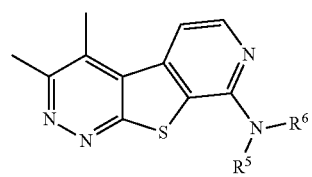

(Ib)

or a pharmaceutically acceptable salt thereof, wherein $R^5$ and $R^6$ are as defined in the embodiments described herein.

In some embodiments, the compound is a compound of formula (Ic):

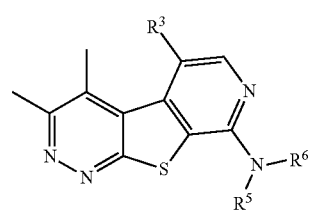

(Ic)

or a pharmaceutically acceptable salt thereof, wherein R³ is selected from hydrogen and halo, and R⁵ and R⁶ are as defined in the embodiments described herein.

In some embodiments, the compound is a compound of formula (Id):

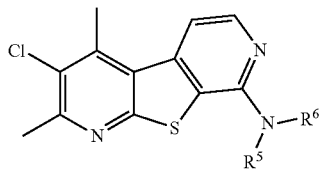

(Id)

or a pharmaceutically acceptable salt thereof,
wherein R⁵ and R⁶ are as defined in the embodiments described herein.

In some embodiments, the compound is a compound of formula (Ie):

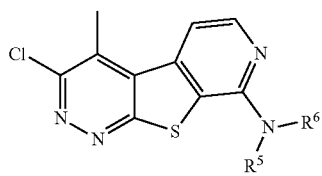

(Ie)

or a pharmaceutically acceptable salt thereof,
wherein R⁵ and R⁶ are as defined in the embodiments described herein.

In some embodiments, the compound is a compound of formula (If):

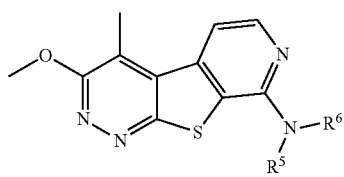

(If)

or a pharmaceutically acceptable salt thereof,
wherein R⁵ and R⁶ are as defined in the embodiments described herein.

In some embodiments, the compound is a compound of formula (Ig):

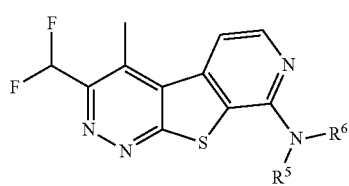

(Ig)

or a pharmaceutically acceptable salt thereof,
wherein R⁵ and R⁶ are as defined in the embodiments described herein.

In some embodiments, R⁵ is hydrogen or alkyl, and R⁶ is selected from the group consisting of alkyl, alkenyl, alkynyl, aryl, heteroaryl, cycloalkyl, heteroalkyl, heterocycle, and —(CR$^b$R$^c$)$_n$—Y, each of which may be optionally substituted.

In some embodiments: R⁵ is selected from hydrogen and methyl; R⁶ is selected from the group consisting of $C_1$-$C_4$ alkyl, $C_3$-$C_6$ cycloalkyl, a 3- to 6-membered heterocycle having one heteroatom selected from N and O, and —(CR$^b$R$^c$)$_n$—Y; n is 1, 2 or 3; R$^b$ and R$^c$ are each hydrogen; Y is selected from the group consisting of —OR, aryl, $C_3$-$C_6$ cycloalkyl, and a 5- to 6-membered heteroaryl having 1 or 2 heteroatoms selected from N, O and S; and R is $C_1$-$C_4$ alkyl; wherein each aryl, cycloalkyl, heteroaryl and heterocycle is independently unsubstituted or substituted with 1 or 2 substituents independently selected from the group consisting of $C_1$-$C_4$ alkyl, $C_1$-$C_4$ hydroxyalkyl, $C_1$-$C_4$ alkoxy, halo, hydroxy, aryl, $C_3$-$C_6$ cycloalkyl, a 3- to 6-membered heterocycle having one heteroatom selected from N and O, and a 5- to 6-membered heteroaryl having 1 or 2 heteroatoms selected from N, O and S.

In some embodiments: R⁵ is hydrogen; R⁶ is selected from the group consisting of $C_1$-$C_4$ alkyl, $C_3$-$C_6$ cycloalkyl, a 3- to 6-membered heterocycle having one heteroatom selected from N and O, and —(CR$^b$R$^c$)$_n$—Y; n is 1; R$^b$ and R$^c$ are each hydrogen; Y is selected from the group consisting of —OR, aryl, $C_3$-$C_6$ cycloalkyl, and a 5- to 6-membered heteroaryl having 1 or 2 heteroatoms selected from N, O and S; and R is $C_1$-$C_4$ alkyl; wherein each aryl, cycloalkyl, heteroaryl and heterocycle is independently unsubstituted or substituted with 1 or 2 substituents independently selected from the group consisting of $C_1$-$C_4$ alkyl, $C_1$-$C_4$ hydroxyalkyl, $C_1$-$C_4$ alkoxy, halo, hydroxy, aryl, $C_3$-$C_6$ cycloalkyl, a 3- to 6-membered heterocycle having one heteroatom selected from N and O, and a 5- to 6-membered heteroaryl having 1 or 2 heteroatoms selected from N, O and S.

In some embodiments: R⁵ is hydrogen; R⁶ is —(CR$^b$R$^c$)$_n$—Y; n is 1; R$^b$ and R$^c$ are each hydrogen; Y is phenyl, which is unsubstituted or substituted with 1 or 2 substituents independently selected from $C_1$-$C_4$ alkyl, $C_1$-$C_4$ haloalkyl, $C_1$-$C_4$ hydroxyalkyl, $C_1$-$C_4$ alkoxy, halo, hydroxy, —OR, and —COR; and each R is independently selected from $C_3$-$C_6$-cycloalkyl-$C_1$-$C_4$-alkyl, and a 3- to 6-membered heterocycle having one or two heteroatoms selected from O, N, and S.

In some embodiments, R⁵ is methyl and R⁶ is methyl.

In some embodiments, R⁵ is hydrogen and R⁶ is a cycloalkyl group selected from cyclopropyl, cyclobutyl, cyclopentyl and cyclohexyl, any of which may be optionally substituted. For example, in some embodiments, R⁶ is a $C_3$-$C_6$ cycloalkyl group that is optionally substituted with 1 or 2 substituents independently selected from $C_1$-$C_4$ alkyl, aryl, and halo. In some embodiments, R⁶ is unsubstituted cyclopropyl, cyclobutyl or cyclopentyl.

In some embodiments, R⁵ is hydrogen and R⁶ is azetidinyl that is substituted with one substituent. In some embodiments, R⁶ is azetidinyl that is substituted with an aryl or a heteroaryl group, wherein the aryl or heteroaryl group may be optionally substituted. In some embodiments, R⁶ is azetidinyl that is substituted with an aryl group, wherein the aryl group may be optionally substituted. In some embodiments, R⁶ is azetidinyl that is substituted with a heteroaryl group, wherein the heteroaryl group may be optionally substituted. In some embodiments, R⁶ is azetidinyl that is substituted with a 5- to 6-membered heteroaryl group having 1, 2 or 3 heteroatoms selected from N, S and O, wherein the heteroaryl group may be optionally substituted. In some embodiments, R⁶ is azetidinyl that is substituted with a phenyl group, a pyridinyl group or a pyrimidinyl group, wherein the phenyl group, the pyridinyl group or the pyrimidinyl group is substituted with one or two substituents independently selected from halo, cyano, $C_1$-$C_4$ alkoxy, and $C_1$-$C_4$ haloalkoxy. In some embodiments, $R^6$ is azetidinyl that is substituted with a pyridinyl group or a pyrimidinyl group, wherein the pyridinyl group or pyrimidinyl group is substituted with one or two substituents independently selected from halo, cyano, $C_1$-$C_4$ alkoxy, and $C_1$-$C_4$ haloalkoxy. In some embodiments, $R^6$ is azetidinyl that is substituted with a pyridinyl group or a pyrimidinyl group, wherein the pyridinyl group or pyrimidinyl group is substituted with one or two substituents independently selected from halo, $C_1$-$C_4$ alkoxy, and $C_1$-$C_4$ haloalkoxy.

In some embodiments, $R^5$ is hydrogen and $R^6$ is —$(CR^bR^c)_n$—Y, wherein Y may be optionally substituted. In some embodiments, $R^b$ and $R^c$ are hydrogen, and n is 1, 2 or 3. In some embodiments, $R^b$ and $R^c$ are hydrogen, and n is 1. In some embodiments, Y is aryl, which may be optionally substituted. In some embodiments, Y is phenyl, which may be optionally substituted. In some embodiments, Y is phenyl substituted with 0, 1 or 2 substituents independently selected from halo, alkoxy, haloalkyl, haloalkoxy, hydroxyalkyl, cycloalkyl, heteroaryl, and —COR. In some embodiments, Y is phenyl substituted with 0, 1 or 2 substituents independently selected from alkoxy, haloalkyl, hydroxyalkyl, haloalkoxy, and —COR, wherein R is a 5- to 6-membered heterocycle having 1, 2 or 3 heteroatoms selected from N, S and O. In some embodiments, Y is phenyl substituted one substituent selected from fluoro, trifluoromethyl, methoxy, trifluoromethoxy, 2-hydroxyisopropyl, and —COR, wherein R is morpholino.

In some embodiments, Y is phenyl substituted with 0, 1 or 2 substituents independently selected from halo, alkoxy, haloalkoxy, hydroxyalkyl, cycloalkyl, heteroaryl, and —COR. In some embodiments, Y is phenyl substituted with 0, 1 or 2 substituents independently selected from alkoxy, haloalkoxy, and —COR, wherein R is a 5- to 6-membered heterocycle having 1, 2 or 3 heteroatoms selected from N, S and O. In some embodiments, Y is phenyl substituted one substituent selected from methoxy, trifluoromethoxy, and —COR, wherein R is morpholino.

In some embodiments, $R^5$ and $R^6$ are taken together with the nitrogen atom to which they are attached to form an azetidinyl, pyrrolidinyl, piperidinyl or piperazinyl group, which may be optionally substituted with 1, 2 or 3 substituents independently selected from the group consisting of alkyl, alkenyl, alkynyl, aryl, heteroaryl, cycloalkyl, heteroalkyl, heterocycle, oxo, and —$(CR^bR^c)_p$—Y, wherein p is 0, 1, 2, 3, 4, 5, 6, 7, or 8. In some embodiments, $R^5$ and $R^6$ are taken together with the nitrogen atom to which they are attached to form an unsubstituted azetidinyl, pyrrolidinyl, piperidinyl or piperazinyl group. In some embodiments, $R^5$ and $R^6$ are taken together with the nitrogen atom to which they are attached to form an unsubstituted pyrrolidine group. In some embodiments, $R^5$ and $R^6$ are taken together with the nitrogen atom to which they are attached to form an unsubstituted azetidinyl, pyrrolidinyl, piperidinyl, piperazinyl, or 2-oxoa-6-azaspiro[3.3]heptanyl group. In some embodiments, $R^5$ and $R^6$ are taken together with the nitrogen atom to which they are attached to form an azetidinyl group that is substituted with a pyridinyl group.

In some embodiments, —$NR^5R^6$ is selected from:

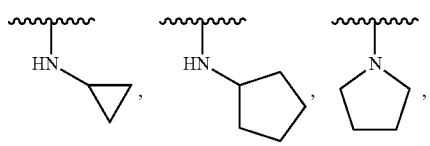

-continued

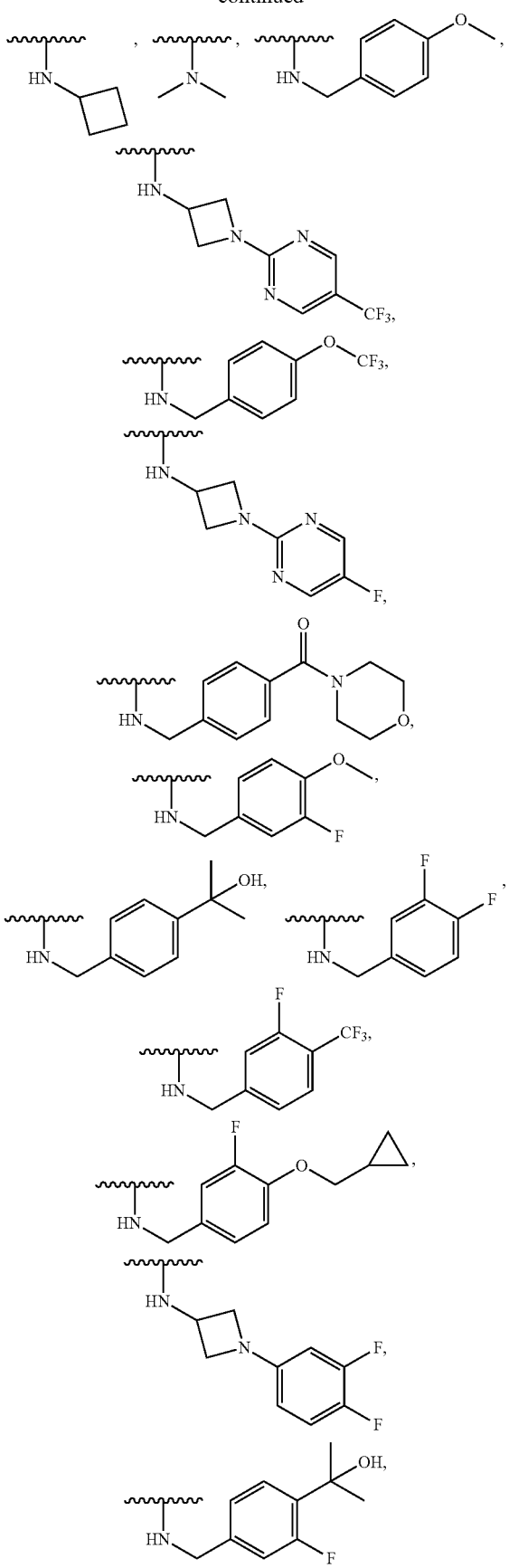

-continued

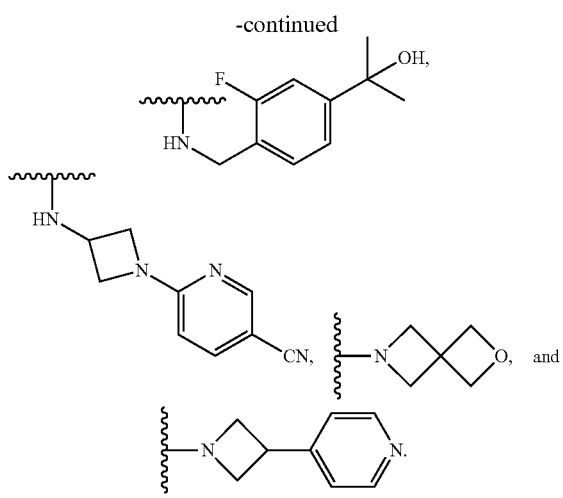

Representative compounds of formula (I) include, but are not limited to:
N-cyclopentyl-2,4-dimethylthieno[2,3-b:5,4-c]dipyridin-8-amine;
2,4-dimethyl-8-(pyrrolidin-1-yl)thieno[2,3-b:5,4-c']dipyridine;
N-cyclobutyl-2,4-dimethylthieno[2,3-b: 5,4-c']dipyridin-8-amine;
N,N,2,4-tetramethylthieno[2,3-b:5,4-c']dipyridin-8-amine;
N-cyclopentyl-3,4-dimethyl-pyrido[4',3':4,5]thieno[2,3-c]pyridazin-8-amine;
3,4-dimethyl-8-pyrrolidin-1-yl-pyrido[4',3':4,5]thieno[2,3-c]pyridazine;
N-cyclobutyl-3,4-dimethyl-pyrido[4',3':4,5]thieno[2,3-c]pyridazin-8-amine;
N-cyclopropyl-3,4-dimethyl-pyrido[4',3':4,5]thieno[2,3-c]pyridazin-8-amine;
N-[(4-methoxyphenyl)methyl]-3,4-dimethyl-pyrido[4',3':4,5]thieno[2,3-c]pyridazin-8-amine;
3,4-dimethyl-N-[1-[5-(trifluoromethyl)pyrimidin-2-yl]azetidin-3-yl]pyrido[4',3':4,5]thieno[2,3-c]pyridazin-8-amine;
3,4-dimethyl-N-[[4-(trifluoromethoxy)phenyl]methyl]pyrido[4',3':4,5]thieno[2,3-c]pyridazin-8-amine;
N-[1-(5-fluoropyrimidin-2-yl)azetidin-3-yl]-3,4-dimethyl-pyrido[4',3':4,5]thieno[2,3-c]pyridazin-8-amine;
[4-[[(3,4-dimethylpyrido[4',3':4,5]thieno[2,3-c]pyridazin-8-yl)amino]methyl]phenyl]-morpholino-methanone;
N-[(3-fluoro-4-methoxy-phenyl)methyl]-3,4-dimethylpyrido[4',3':4,5]thieno[2,3-c]pyridazin-8-amine;
2-[4-[[(3,4-dimethylpyrido[4',3': 4,5]thieno[2,3-c]pyridazin-8-yl)amino]methyl]phenyl]propan-2-ol;
N-[(3,4-difluorophenyl)methyl]-3,4-dimethyl-pyrido[4',3':4,5]thieno[2,3-c]pyridazin-8-amine;
N-[[3-fluoro-4-(trifluoromethyl)phenyl]methyl]-3,4-dimethyl-pyrido[4',3':4,5]thieno[2,3-c]pyridazin-8-amine;
N-[[4-(cyclopropylmethoxy)-3-fluoro-phenyl]methyl]-3,4-dimethyl-pyrido[4',3':4,5]thieno[2,3-c]pyridazin-8-amine;
N-[1-(3,4-difluorophenyl)azetidin-3-yl]-3,4-dimethyl-pyrido[4',3':4,5]thieno[2,3-c]pyridazin-8-amine;
2-[4-[[(3,4-dimethylpyrido[4',3': 4,5]thieno[2,3-c]pyridazin-8-yl)amino]methyl]-2-fluoro-phenyl]propan-2-ol;
2-[4-[[(3,4-dimethylpyrido[4',3': 4,5]thieno[2,3-c]pyridazin-8-yl)amino]methyl]-3-fluoro-phenyl]propan-2-ol;
6-[3-[(3,4-dimethylpyrido[4',3': 4,5]thieno[2,3-c]pyridazin-8-yl)amino]azetidin-1-yl]pyridine-3-carbonitrile; and
5-chloro-3,4-dimethyl-8-pyrrolidin-1-yl-pyrido[4',3':4,5]thieno[2,3-c]pyridazine;
2,4-dimethyl-N-(1-(5-(trifluoromethyl)pyrimidin-2-yl)azetidin-3-yl)thieno[2,3-b: 5,4-c']dipyridin-8-amine;
N-(3-fluoro-4-methoxybenzyl)-2,4-dimethylthieno[2,3-b:5,4-c']dipyridin-8-amine;
2-(4-(((2,4-dimethylthieno[2,3-b:5,4-c]dipyridin-8-yl)amino)methyl)phenyl)propan-2-ol;
2-(4-(((2,4-dimethylthieno[2,3-b:5,4-c]dipyridin-8-yl)amino)methyl)-3-fluorophenyl)propan-2-ol;
3-chloro-N-(4-methoxybenzyl)-2,4-dimethylthieno[2,3-b:5,4-c']dipyridin-8-amine;
2-(4-(((3-chloro-2,4-dimethylthieno[2,3-b: 5,4-c]dipyridin-8-yl)amino)methyl)phenyl)propan-2-ol;
3-chloro-2,4-dimethyl-8-(pyrrolidin-1-yl)thieno[2,3-b: 5,4-c']dipyridine;
2-(4-(((3-chloro-2,4-dimethylthieno[2,3-b: 5,4-c']dipyridin-8-yl)amino)methyl)-2-fluorophenyl)propan-2-ol;
3-chloro-N-(4-methoxybenzyl)-4-methylpyrido[4',3':4,5]thieno[2,3-c]pyridazin-8-amine;
3-chloro-4-methyl-N-(1-(5-(trifluoromethyl)pyrimidin-2-yl)azetidin-3-yl)pyrido[4',3':4,5]thieno[2,3-c]pyridazin-8-amine;
3-chloro-N-cyclobutyl-4-methylpyrido[4',3':4,5]thieno[2,3-c]pyridazin-8-amine;
3-chloro-4-methyl-8-(pyrrolidin-1-yl)pyrido[4',3':4,5]thieno[2,3-c]pyridazine;
3-chloro-N-(3-fluoro-4-methoxybenzyl)-4-methylpyrido[4',3:4,5]thieno[2,3-c]pyridazin-8-amine;
3-Methoxy-N-(4-methoxybenzyl)-4-methylpyrido[4',3':4,5]thieno[2,3-c]pyridazin-8-amine;
3-methoxy-4-methyl-N-(1-(5-(trifluoromethyl)pyrimidin-2-yl)azetidin-3-yl)pyrido[4',3':4,5]thieno[2,3-c]pyridazin-8-amine;
N-cyclobutyl-3-methoxy-4-methylpyrido[4',3':4,5]thieno[2,3-c]pyridazin-8-amine;
3-(difluoromethyl)-4-methyl-8-(pyrrolidin-1-yl)pyrido[4',3':4,5]thieno[2,3-c]pyridazine;
6-(3-(difluoromethyl)-4-methylpyrido[4',3':4,5]thieno[2,3-c]pyridazin-8-yl)-2-oxa-6-azaspiro[3.3]heptane; and
3-(difluoromethyl)-4-methyl-8-(3-(pyridin-4-yl)azetidin-1-yl)pyrido[4',3':4,5]thieno[2,3-c]pyridazine,
or a pharmaceutically acceptable salt thereof.

Compound names are assigned by using the Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

In some embodiments, the compound of formula (I) is isotopically labeled. In some embodiments, any hydrogen atom in a compound of formula (I) may be deuterium. In some embodiments, $R^2$ is deuterium.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

In some embodiments, a compound of formula (I) is provided as a hydrochloride salt or a dihydrochloride salt. In some embodiments, a compound of formula (I) is provided as a trifluoroacetic acid salt.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations used in the Schemes that follow are: Ac is acetyl or acetate; DAST is diethylaminosulfur trifluoride; DCE is 1,2-dichloroethane; DCM is dichloromethane; DIEA is N,N-diisopropylethylamine; DMF is N,N-dimethylformamide; dppf is 1,1'-bis(diphenylphosphino)ferrocene; HATU is 1-[bis(dimethylamino)methylene]-1H-1,2,3-triazolo[4,5-b]pyridinium 3-oxid hexafluorophosphate; IPA is isopropyl alcohol; MeCN is acetonitrile; MeOH is methanol; MW is microwave (referring to a microwave reactor); NBS is N-bromosuccinimide; NCS is N-chlorosuccinimide; NMP is N-methyl-2-pyrrolidone; rt and r.t. are room temperature; tBuOH is tert-butanol; tBuONO is tert-butyl nitrite; TEA is triethylamine; TFA is trifluoroacetic acid; TFAA is trifluoroacetic anhydride; and THF is tetrahydrofuran.

Compounds of formula (I), specifically compounds of formula (Ia), (Ib), (Ic), (Id), (Ie), (If), and (Ig), can be synthesized as shown in Schemes 1-7.

Scheme 1

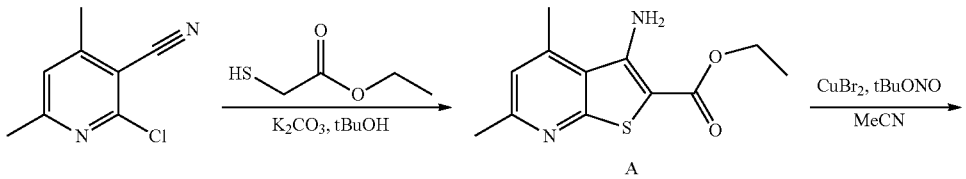

A

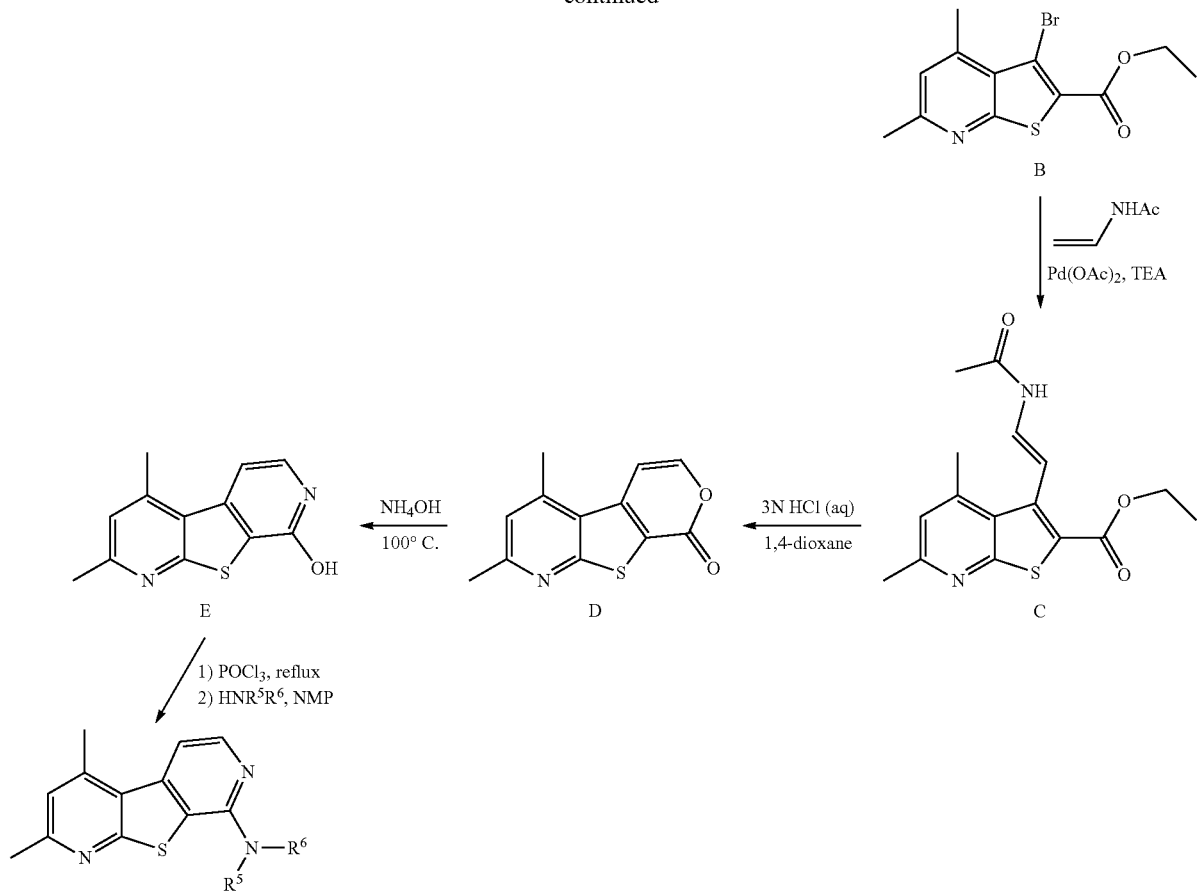

As shown in Scheme 1, 2-chloro-4,6-dimethyl-3-pyridinecarbonitrile can be reacted with ethyl thioglycolate to provide compound A, which can be reacted with cupric bromide and tert-butyl nitrite to provide compound B. Reaction of compound B with N-vinylacetamide in the presence of a palladium catalyst such as palladium acetate provides compound C, which can be reacted with an acid such as hydrochloric acid to provide compound D. Reaction with ammonium hydroxide produces compound E. Finally, reaction with phosphorus oxychloride followed by coupling with an appropriate amine provides a compound of formula (Ia).

Scheme 2

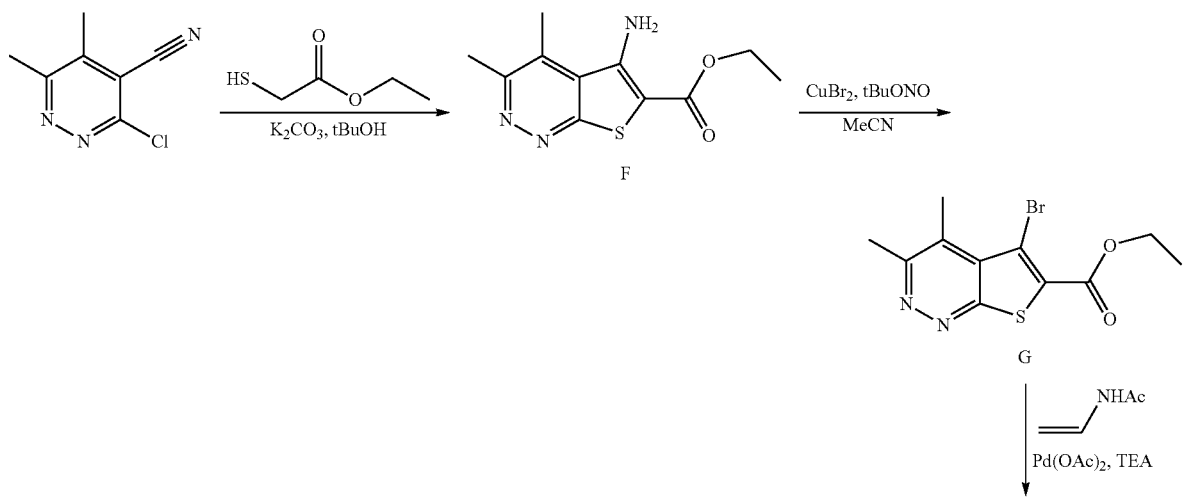

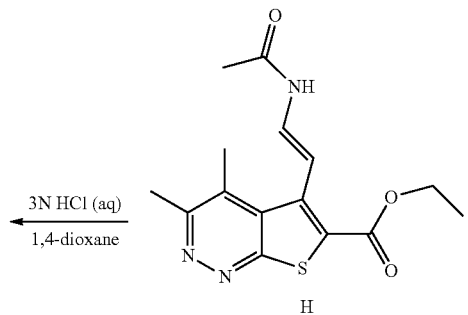

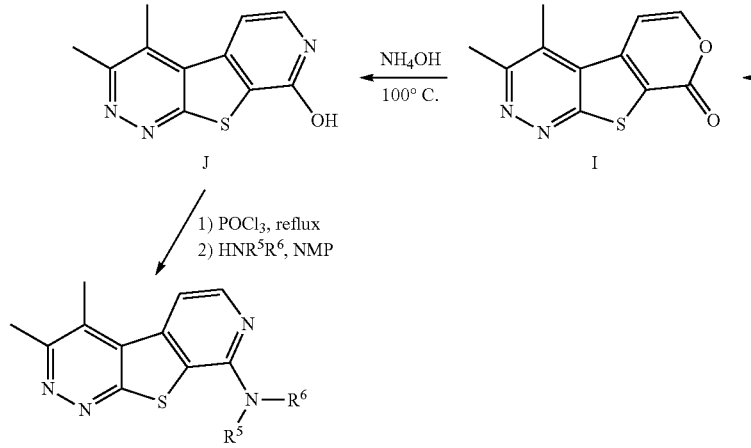

As shown in Scheme 2, reaction of 3-chloro-5,6-dimethylpyridazine-4-carbonitrile with ethyl thioglycolate can provide compound F, which can be reacted with cupric bromide and tert-butyl nitrite to provide compound G. Reaction of compound G with N-vinylacetamide in the presence of a palladium catalyst such as palladium acetate provides compound H, which can be reacted with an acid such as hydrochloric acid to provide compound I. Reaction with ammonium hydroxide produces compound J. Finally, reaction with phosphorus oxychloride followed by coupling with an appropriate amine provides a compound of formula (Ib).

by coupling with an appropriate amine to provide a compound of formula (Ic) wherein $R^3$ is chloro.

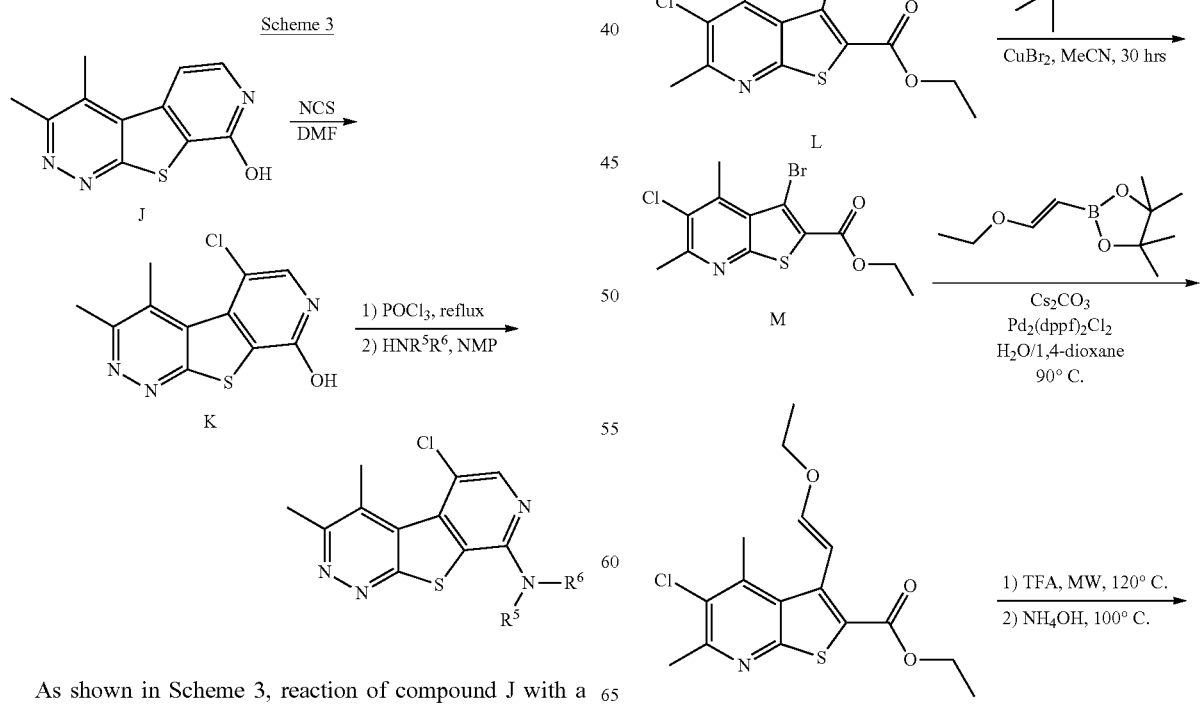

As shown in Scheme 3, reaction of compound J with a chlorinating agent such as NCS can provide compound K, which can be reacted with phosphorus oxychloride followed -continued

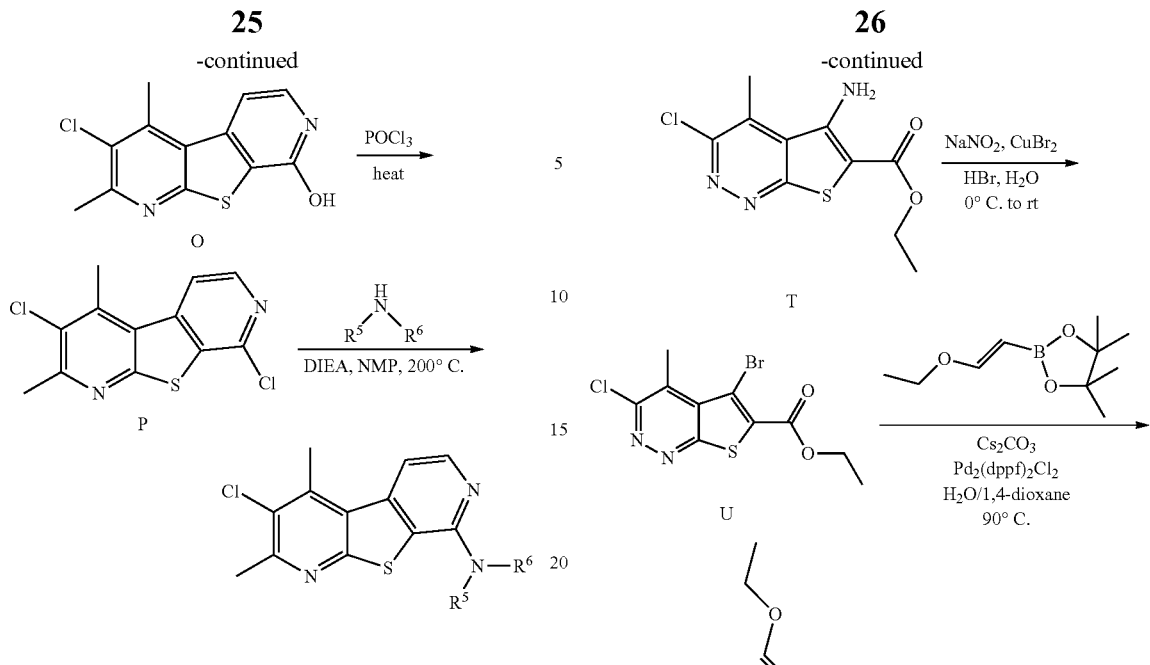

As shown in Scheme 4, reaction of 2,5-dichloro-4,6-dimethylnicotinonitrile with ethyl thioglycolate can provide compound L, which can be reacted with tert-butyl nitrite in the presence of cupric bromide to provide compound M. Coupling with (E)-1-ethoxyethene-2-boronic acid pinacol ester provides compound N, which can be reacted with an acid such as TFA followed by reaction with ammonium hydroxide to provide compound O. Finally, reaction with phosphorus oxychloride provides compound P, and coupling with an appropriate amine provides a compound of formula (Id).

Scheme 5

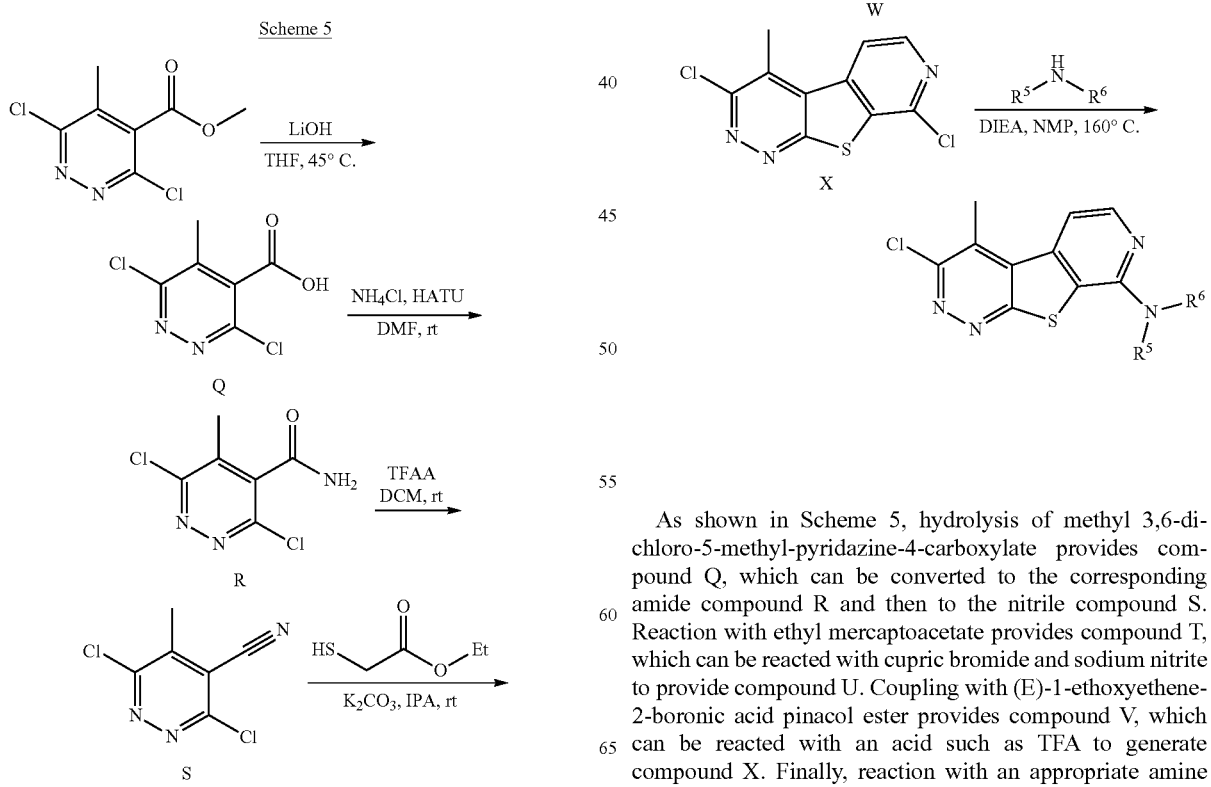

As shown in Scheme 5, hydrolysis of methyl 3,6-dichloro-5-methyl-pyridazine-4-carboxylate provides compound Q, which can be converted to the corresponding amide compound R and then to the nitrile compound S. Reaction with ethyl mercaptoacetate provides compound T, which can be reacted with cupric bromide and sodium nitrite to provide compound U. Coupling with (E)-1-ethoxyethene-2-boronic acid pinacol ester provides compound V, which can be reacted with an acid such as TFA to generate compound X. Finally, reaction with an appropriate amine can provide a compound of formula (Ie).

Scheme 6

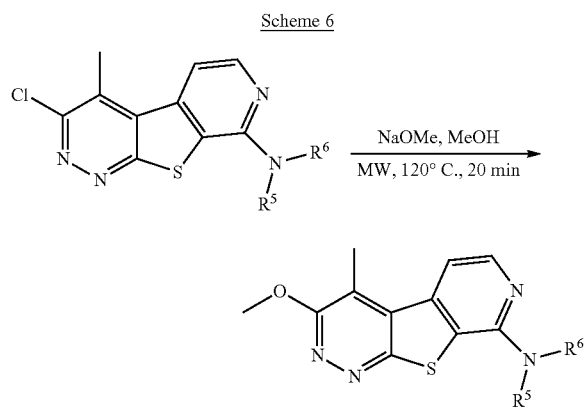

As shown in Scheme 6, a compound of formula (Ie) can be converted to a compound of formula (If) by reaction with sodium methoxide in methanol.

Finally, as shown in Scheme 7, compound G (prepared as shown in Scheme 2) can be brominated and then reacted with potassium acetate to form compound Y, which can be deacetylated to form compound Z. Oxidation with manganese dioxide followed by reaction with DAST provides compound AA, which can be coupled with (E)-1-ethoxyethene-2-boronic acid pinacol ester to provide compound BB. Reaction with ammonium hydroxide followed by phosphorus oxychloride provides compound CC. Finally reaction with an appropriate amine can provide a compound of formula (Ig).

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation

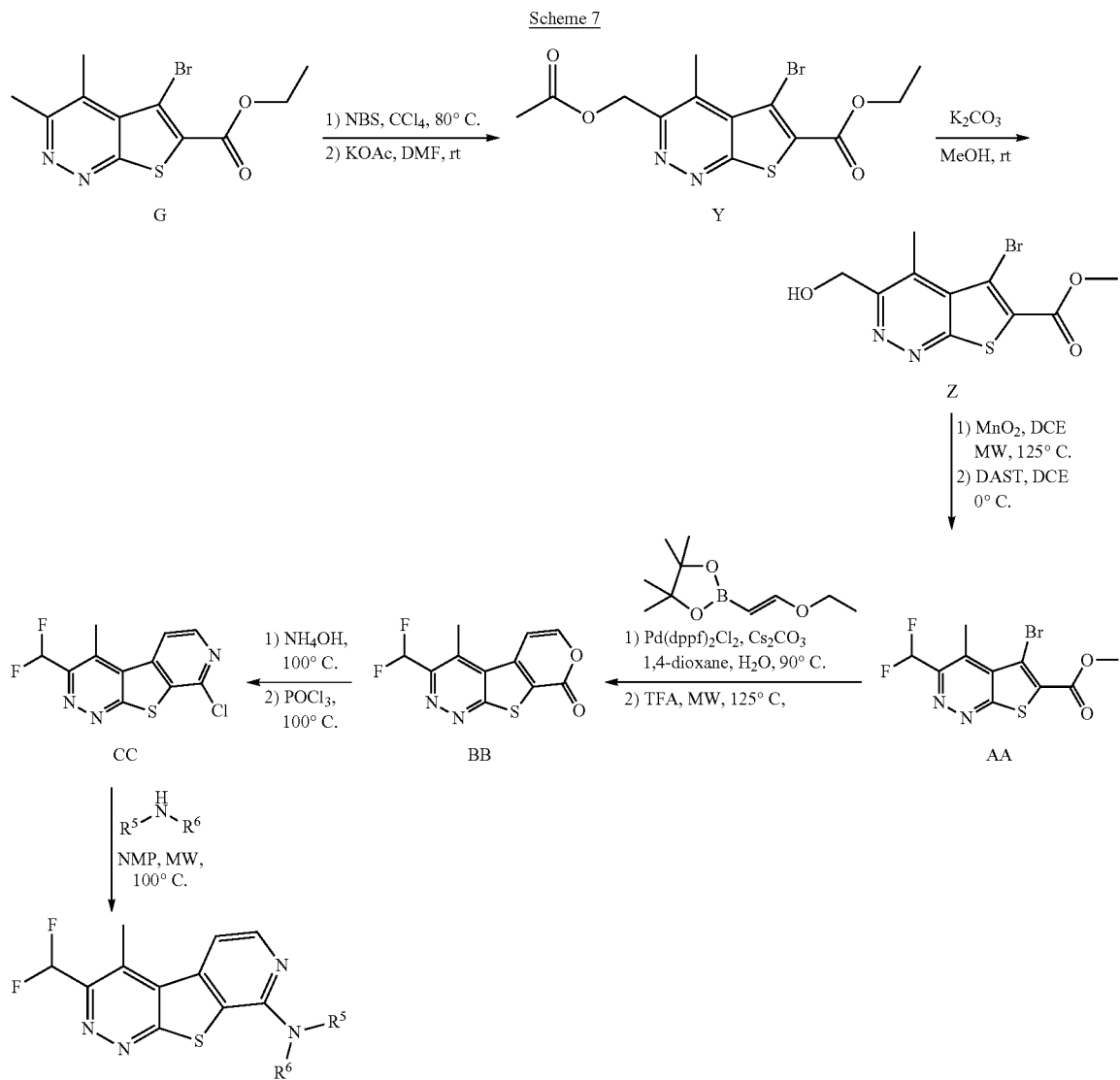

under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity

In some embodiments, the disclosed compounds potentiate the agonist response (e.g., acetylcholine) of mAChR $M_4$. In some embodiments, the disclosed compounds increase mAChR $M_4$ response to non-maximal concentrations of agonist in the presence of compound compared to the response to agonist in the absence of compound. The potentiation of mAChR $M_4$ activity can be demonstrated by methodology known in the art. For example, activation of mAChR $M_4$ activity can be determined by measurement of calcium flux in response to agonist, e.g. acetylcholine, in cells loaded with a $Ca^{2+}$-sensitive fluorescent dye (e.g., Fluo-4) and co-expression of a chimeric or promiscuous G protein. In some embodiments, the calcium flux was measured as an increase in fluorescent static ratio. In some embodiments, positive allosteric modulator activity was analyzed as a concentration-dependent increase in the $EC_{20}$ acetylcholine response (i.e. the response of mAChR $M_4$ at a concentration of acetylcholine that yields 20% of the maximal response).

In some embodiments, the disclosed compounds activate mAChR $M_4$ response as an increase in calcium fluorescence in mAChR $M_4$-transfected CHO-K1 cells in the presence of the compound, compared to the response of equivalent CHO-K1 cells in the absence of the compound. In some embodiments, a disclosed compound activates the mAChR $M_4$ response with an $EC_{50}$ of less than about 10 μM, less than about 5 μM, less than about 1 μM, less than about 500 nM, of less than about 100 nM, or less than about 50 nM. In some embodiments, the mAChR $M_4$-transfected CHO-K1 cells are transfected with human mAChR $M_4$ In some embodiments, the mAChR $M_4$-transfected CHO-K1 cells are transfected with rat mAChR $M_4$.

The disclosed compounds may exhibit positive allosteric modulation of mAChR $M_4$ response to acetylcholine as an increase in response to non-maximal concentrations of acetylcholine in CHO-K1 cells transfected with a mAChR $M_4$ in the presence of the compound, compared to the response to acetylcholine in the absence of the compound. In some embodiments, the disclosed compounds exhibit positive allosteric modulation of the mAChR $M_4$ response to acetylcholine with an $EC_{50}$ of less than about 10 μM, less than about 5 μM, less than about 1 μM, less than about 500 nM, or less than about 100 nM. In some embodiments, the $EC_{50}$ for positive allosteric modulation is determined in CHO-K1 cells are transfected with a mAChR $M_4$. In some embodiments, the mAChR $M_4$ transfected human mAChR $M_4$. In some embodiments, the mAChR $M_4$ transfected rat mAChR $M_4$.

The disclosed compounds may activate mAChR $M_4$ response in mAChR $M_4$-transfected CHO-K1 cells with an $EC_{50}$ less than the $EC_{50}$ for one or more of mAChR $M_1$, $M_2$, $M_3$ or $M_5$-transfected CHO-K1 cells. That is, a disclosed compound can have selectivity for the mAChR $M_4$ receptor vis-à-vis one or more of the mAChR $M_1$, $M_2$, $M_3$ or $M_5$ receptors. For example, in some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_1$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, a disclosed compound can activate mAChR $M_4$ response with an $EC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, or greater than about 500-fold less than that for the mAChR $M_1$, $M_2$, $M_3$, or $M_5$ receptors.

The disclosed compounds may activate mAChR $M_4$ response in $M_4$-transfected CHO-K1 cells with an $EC_{50}$ of less than about 10 μM and exhibits a selectivity for the $M_4$ receptor vis-à-vis one or more of the mAChR $M_1$, $M_2$, $M_3$, or $M_5$ receptors. For example, in some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with an $EC_{50}$ of about 5-fold less, 10-fold less, 20-fold less, 30-fold less, 50-fold less, 100-fold less, 200-fold less, 300-fold less, 400-fold less, or greater than about 500-fold less than that for mAChR $M_1$. In some embodiments, the compound can have an $EC_{50}$ of less than about 10 μM, of less than about M, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with $EC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, $M_2$, $M_3$, or $M_5$ receptors, or greater than about 500-fold less than that for the mAChR $M_1$, $M_2$, $M_3$, or $M_5$ receptors.

In vivo efficacy for disclosed compounds can be measured in a number of preclinical rat behavioral models where known, clinically useful antipsychotics display similar positive responses. For example, disclosed compounds may reverse amphetamine-induced hyperlocomotion in male Sprague-Dawley rats at doses ranging from 1 to 100 mg/kg p.o.

3. PHARMACEUTICAL COMPOSITIONS AND FORMULATIONS

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition or formulation may exhibit positive allosteric modulation of mAChR $M_4$ with an $EC_{50}$ of less than about 10 µM, less than about 5 µM, less than about 1 µM, less than about 500 nM, or less than about 100 nM. The pharmaceutical composition or formulation may exhibit positive allosteric modulation of mAChR M4 with an $EC_{50}$ of between about 10 µM and about 1 nM, about 1 µM and about 1 nM, about 100 nM and about 1 nM, or between about 10 nM and about 1 nM.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I).

4. METHODS OF USE

The disclosed compounds, pharmaceutical compositions and formulations may be used in methods for treatment of disorders, such as neurological and/or psychiatric disorders, associated with muscarinic acetylcholine receptor dysfunction. The disclosed compounds and pharmaceutical compositions may also be used in methods for the potentiation of muscarinic acetylcholine receptor activity in a mammal, and in methods for enhancing cognition in a mammal. The methods further include cotherapeutic methods for improving treatment outcomes in the context of cognitive or behavioral therapy. In the methods of use described herein, additional therapeutic agent(s) may be administered simultaneously or sequentially with the disclosed compounds and compositions.

a. Treating Disorders

The disclosed compounds, pharmaceutical compositions and formulations may be used in methods for treatment of disorders, such as neurological and/or psychiatric disorders, associated with muscarinic acetylcholine receptor dysfunction. The methods of treatment may comprise administering to a subject in need of such treatment a therapeutically effective amount of the compound of formula (I), or a pharmaceutical composition comprising a therapeutically effective amount of a compound of formula (I).

In some embodiments, the disclosure provides to a method for enhancing cognition in a mammal comprising the step of administering to the mammal a therapeutically effective amount of the compound of formula (I), or a pharmaceutical composition comprising a therapeutically effective amount of a compound of formula (I).

The compounds and compositions disclosed herein may be useful for treating, preventing, ameliorating, controlling or reducing the risk of a variety of disorders associated with selective mAChR $M_4$ receptor activation. For example, a treatment can include selective mAChR $M_4$ receptor activation to an extent effective to affect cholinergic activity. A disorder can be associated with cholinergic activity, for example cholinergic hypofunction. Thus, provided is a method of treating or preventing a disorder in a subject comprising the step of administering to the subject at least one disclosed compound or at least one disclosed pharmaceutical composition, in an amount effective to treat the disorder in the subject.

Also provided is a method for the treatment of one or more disorders associated with mAChR $M_4$ receptor activity in a subject comprising the step of administering to the subject a therapeutically effective amount of the compound of formula (I), or a pharmaceutical composition comprising a therapeutically effective amount of a compound of formula (I).

In some embodiments, the disclosure provides a method for the treatment of a disorder associated with muscarinic acetylcholine receptor dysfunction in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, the disclosed compounds and compositions have utility in treating a variety of neurological, psychiatric and cognitive disorders associated with the mAChR $M_4$ receptor, including one or more of the following conditions or diseases: schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In some embodiments, the psychotic disorder is a psychosis associated with an illness selected from major depressive disorder, affective disorder, bipolar disorder, electrolyte disorder, Alzheimer's disease, neurological disorder, hypoglycemia, AIDS, lupus, and post-traumatic stress disorder.

In some embodiments, the disorder is a neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In some embodiments, the disorder is a psychotic disorder is selected from schizophrenia, brief psychotic disorder, schizophreniform disorder, schizoaffective disorder, delusional disorder, and shared psychotic disorder. In some embodiments, the schizophrenia is selected from catastrophic schizophrenia, catatonic schizophrenia, paranoid schizophrenia, residual schizophrenia, disorganized schizophrenia, and undifferentiated schizophrenia. In some embodiments, the disorder is selected from schizoid personality disorder, schizotypal personality disorder, and paranoid personality disorder. In some embodiments, the psychotic disorder is due to a general medical condition and is substance-induced or drug-induced (phencyclidine, ketamine and other dissociative anesthetics, amphetamine and other psychostimulants, and cocaine).

In some embodiments, the present disclosure provides a method for treating a cognitive disorder, comprising administering to a patient in need thereof an effective amount of a compound or a composition of the present disclosure. In some embodiments, cognitive disorders include dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse), delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

The text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. The fifth edition of the Diagnostic and Statistical Manual of Mental Disorders (DSM-5) (2013, American Psychiatric Association, Washington D.C.) provides a diagnostic tool for neurocognitive disorders (NCDs) that include delirium, followed by the syndromes of major NCD, mild NCD, and their etiological subtypes. The major or mild NCD subtypes include NCD due to Alzheimer's disease, vascular NCD, NCD with Lewy bodies, NCD due to Parkinson's disease, frontotemporal NCD, NCD due to traumatic brain injury, NCD due to HIV infection, substance/medication-induced NCD, NCD due to Huntington's disease, NCD due to prion disease, NCD due to another medical condition, NCD due to multiple etiologies, and unspecified NCD. The NCD category in DSM-5 encompasses the group of disorders in which the primary clinical deficit is in cognitive function, and that are acquired rather than developmental. As used herein, the term "cognitive disorders" includes treatment of those cognitive disorders and neurocognitive disorders as described in DSM-IV-TR or DSM-5. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In some embodiments, the present disclosure provides a method for treating schizophrenia or psychosis, comprising administering to a patient in need thereof an effective amount of a compound or composition of the present disclosure. Particular schizophrenia or psychosis pathologies are paranoid, disorganized, catatonic or undifferentiated schizophrenia and substance-induced psychotic disorder. DSM-IV-TR provides a diagnostic tool that includes paranoid, disorganized, catatonic, undifferentiated or residual schizophrenia, and substance-induced psychotic disorder. DSM-5 eliminated the subtypes of schizophrenia, and instead includes a dimensional approach to rating severity for the core symptoms of schizophrenia, to capture the heterogeneity in symptom type and severity expressed across individuals with psychotic disorders. As used herein, the term "schizophrenia or psychosis" includes treatment of those mental disorders as described in DSM-IV-TR or DSM-5. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In some embodiments, the present disclosure provides a method for treating pain, comprising administering to a patient in need thereof an effective amount of a compound or composition of the present disclosure. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

The compounds and compositions may be further useful in a method for the prevention, treatment, control, amelioration, or reduction of risk of the diseases, disorders and conditions noted herein. The compounds and compositions may be further useful in a method for the prevention, treatment, control, amelioration, or reduction of risk of the aforementioned diseases, disorders and conditions, in combination with other agents.

In the treatment of conditions which require activation of mAChR $M_4$, an appropriate dosage level may be about 0.01 to 500 mg per kg patient body weight per day, which can be administered in single or multiple doses. The dosage level may be about 0.1 to about 250 mg/kg per day, or about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the disclosure relates to a method for activating mAChR $M_4$ receptor activity in at least one cell, comprising the step of contacting the at least one cell with at least one disclosed compound or at least one product of a disclosed method in an amount effective to activate mAChR $M_4$ in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for activating mAChR $M_4$ activity in a subject, comprising the step of administering to the subject at least one disclosed compound or at least one product of a disclosed method in a dosage and amount effective to activating mAChR $M_4$ activity in the subject. In some embodiments, the subject is mammalian, for example, human. In some embodiments, the mammal has been diagnosed with a need for mAChR $M_4$ agonism prior to the administering step. In some embodiments, the mammal has been diagnosed with a need for mAChR $M_4$ activation prior to the administering step. In some embodiments, the method further comprises the step of identifying a subject in need of mAChR $M_4$ agonism.

In some embodiments, the invention relates to a method for the treatment of a disorder associated with selective mAChR $M_4$ activation, for example, a disorder associated with cholinergic activity, in a mammal comprising the step of administering to the mammal at least one disclosed compound or at least one product of a disclosed method in a dosage and amount effective to treat the disorder in the mammal. In some embodiments, the mammal is a human. In some embodiments, the mammal has been diagnosed with a need for treatment for the disorder prior to the administering step. In some embodiments, the method further comprises the step of identifying a subject in need of treatment for the disorder.

In some embodiments, the disorder can be selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

In some embodiments, the disorder is Alzheimer's disease.

b. Potentiation of Muscarinic Acetylcholine Receptor Activity

In some embodiments, the disclosure relates to a method for potentiation of muscarinic acetylcholine receptor activity in a mammal comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, potentiation of muscarinic acetylcholine receptor activity increases muscarinic acetylcholine receptor activity. In some embodiments, potentiation of muscarinic acetylcholine receptor activity is partial agonism of the muscarinic acetylcholine receptor. In some embodiments, potentiation of muscarinic acetylcholine receptor activity is positive allosteric modulation of the muscarinic acetylcholine receptor.

In some embodiments, the compound administered exhibits potentiation of mAChR $M_4$ with an $EC_{50}$ of less than about 10 µM, less than about 5 µM, less than about 1 µM, less than about 500 nM, or less than about 100 nM. In some embodiments, the compound administered exhibits potentiation of mAChR $M_4$ with an $EC_{50}$ of between about 10 µM and about 1 nM, about 1 µM and about 1 nM, about 100 nM and about 1 nM, or about 10 nM and about 1 nM.

In some embodiments, the mammal is a human. In some embodiments, the mammal has been diagnosed with a need for potentiation of muscarinic acetylcholine receptor activity prior to the administering step. In some embodiments, the method further comprises the step of identifying a mammal in need of potentiating muscarinic acetylcholine receptor activity. In some embodiments, the potentiation of muscarinic acetylcholine receptor activity treats a disorder associated with muscarinic acetylcholine receptor activity in the mammal. In some embodiments, the muscarinic acetylcholine receptor is mAChR $M_4$.

In some embodiments, potentiation of muscarinic acetylcholine receptor activity in a mammal is associated with the treatment of a neurological and/or psychiatric disorder associated with a muscarinic receptor dysfunction, such as a neurological or psychiatric disorder disclosed herein. In some embodiments, the muscarinic receptor is mAChR $M_4$.

In some embodiments, the disclosure provides to a method for potentiation of muscarinic acetylcholine receptor activity in a cell, comprising the step of contacting the cell with an effective amount of at least one disclosed compound or a pharmaceutically acceptable salt thereof. In some embodiments, the cell is mammalian (e.g., human). In some embodiments, the cell has been isolated from a mammal prior to the contacting step. In some embodiments, contacting is via administration to a mammal.

c. Enhancing Cognition

In some embodiments, the invention relates to a method for enhancing cognition in a mammal comprising the step of administering to the mammal an effective amount of least one disclosed compound; or a pharmaceutically acceptable salt, hydrate, solvate, or polymorph thereof.

In some embodiments, the mammal is a human. In some embodiments, the mammal has been diagnosed with a need for cognition enhancement prior to the administering step. In some embodiments, the method further comprises the step of identifying a mammal in need of cognition enhancement. In some embodiments, the need for cognition enhancement is associated with a muscarinic receptor dysfunction. In some embodiments, the muscarinic receptor is mAChR $M_4$.

In some embodiments, the cognition enhancement is a statistically significant increase in Novel Object Recognition. In some embodiments, the cognition enhancement is a statistically significant increase in performance of the Wisconsin Card Sorting Test.

d. Cotherapeutic Methods

The present invention is further directed to administration of a selective mAChR $M_4$ activator for improving treatment outcomes in the context of cognitive or behavioral therapy. That is, in some embodiments, the invention relates to a cotherapeutic method comprising a step of administering to a mammal an effective amount and dosage of at least one disclosed compound, or a pharmaceutically acceptable salt thereof.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

e. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In some embodiments, the compound can be employed in combination with anti-Alzheimer's agents, beta-secretase inhibitors, cholinergic agents, gamma-secretase inhibitors, HMG-CoA reductase inhibitors, $M_1$ allosteric agonists, $M_1$ positive allosteric modulators, NSAIDs including ibuprofen, vitamin E, and anti-amyloid antibodies. In another embodiment, the subject compound can be employed in combination with sedatives, hypnotics, anxiolytics, antipsychotics (typical and atypical), antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound can be administered in conjunction with the use of physical methods such as with light therapy or electrical stimulation.

In some embodiments, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In some embodiments, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In some embodiments, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In some embodiments, the compounds can be coadministered with orthosteric muscarinic agonists, muscarinic potentiators, or cholinesterase inhibitors. In some embodiments, the compounds can be coadministered with GlyT1 inhibitors and the like such as, but not limited to: risperidone, clozapine, haloperidol, fluoxetine, prazepam, xanomeline, lithium, phenobarbitol, and salts thereof and combinations thereof.

f. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. KITS

In one aspect, the disclosure provides kits comprising at least one disclosed compound or a pharmaceutically acceptable salt thereof, and one or more of:
  (a) at least one agent known to increase mAChR $M_4$ activity;
  (b) at least one agent known to decrease mAChR $M_4$ activity;
  (c) at least one agent known to treat a disorder associated with cholinergic activity;
  (d) instructions for treating a disorder associated with cholinergic activity;
  (e) instructions for treating a disorder associated with $M_4$ receptor activity; or
  (f) instructions for administering the compound in connection with cognitive or behavioral therapy.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may f information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. EXAMPLES

All NMR spectra were recorded on a 400 MHz AMX Bruker NMR spectrometer. 1H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Abbreviations used in the schemes and Examples that follow are: Ac is acetyl or acetate; DAST is diethylamino-sulfur trifluoride; DCE is 1,2-dichloroethane; DCM is dichloromethane; DIEA and DIPEA both refer to N,N-diisopropylethylamine; DMF is N,N-dimethylformamide; dppf is 1,1'-bis(diphenylphosphino)ferrocene; eq. refers to equivalents; HATU is 1-[bis(dimethylamino)methylene]-1H-1,2,3-triazolo[4,5-b]pyridinium 3-oxid hexafluorophosphate; IPA is isopropyl alcohol; MeCN is acetonitrile; MeOH is methanol; MW is microwave (referring to a microwave reactor); NBS is N-bromosuccinimide; NCS is N-chlorosuccinimide; NMP is N-methyl-2-pyrrolidone; rt and r.t. are room temperature; tBuOH is tert-butanol; tBuONO is tert-butyl nitrite; TEA is triethylamine; TFA is trifluoroacetic acid; TFAA is trifluoroacetic anhydride; and THF is tetrahydrofuran.

Example 1. General Amine Synthesis

The following is an exemplary syntheses of an amine used to prepare a compound disclosed herein, (S)-3-(pyrrolidin-3-yloxy)pyridine (X2).

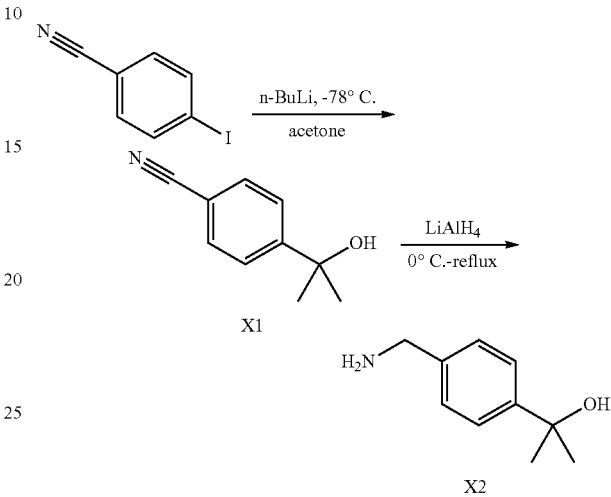

4-(2-Hydroxypropan-2-yl)benzonitrile (X1)

To a solution of 4-iodobenzonitrile (10.0 g, 43.7 mmol, 1.0 eq.) in THF (218 mL) at −78° C. was added n-butyl lithium (2.5 M in hexanes, 22.7 mL, 56.8 mmol, 1.3 eq.) dropwise as to maintain the temperature below −70° C. After 1 h, acetone (32.0 mL, 436.6 mmol, 10.0 eq.) was added while maintaining the temperature below −70° C. The dry ice bath was removed. After 16 hours at RT, a saturated solution of NH$_4$Cl (100 mL) was added, followed by EtOAc (250 mL). The layers were separated. The aqueous layer was extracted with EtOAc (2×200 mL). The combined organic layers were washed with brine, dried (Na$_2$SO$_4$), filtered and concentrated. The residue was purified by flash column chromatography on silica gel (0-60% EtOAc/hexanes) to provide the title compound as a viscous oil (4.88 g, 69% yield). ES-MS [M+1]$^+$: 162.4; $^1$H NMR (400 MHz, DMSO-d$_6$) δ 7.76 (dd, J=10, 2 Hz, 2H), 7.66 (dd, J=8.6, 2 Hz, 2H), 5.28 (s, 1H), 1.43 (s, 6H).

2-(4-(Aminomethyl)phenyl)propan-2-ol (X2)

To a solution of 4-(2-hydroxypropan-2-yl)benzonitrile (4.88 g, 30.3 mmol, 1.0 eq.) in THF (200 mL) was added a solution of lithium aluminum hydride (2.0 M in THF, 45.4 mL, 90.8 mmol) dropwise at 0° C. After 30 minutes at 0° C., the ice bath was removed and the reaction was heated to reflux. After 30 minutes, a creamy paste was formed. The heat was removed. At 0° C., a saturated solution of Rochelle salt (50 mL) was added slowly followed by MeOH (50 mL). The mixture was stirred at RT for 1 h and filtered through a pad of Celite which was further rinsed with 15% MeOH in DCM. The collected filtrate was dried (MgSO$_4$), filtered and concentrated. The residue was purified by flash column chromatography on silica gel using a solution of DCM/MeOH/NH$_4$OH (89:10:1) with DCM as a co-solvent to provide the title compound as a white crystalline solid (4.25 g, 85% yield). ES-MS [M+1]$^+$: 166.3; $^1$H NMR (400 MHz, DMSO-d$_6$) δ 7.38 (d, J=8.3 Hz, 2H), 7.24 (d, J=8.4 Hz, 2H), 4.93 (bs, 1H), 3.68 (s, 2H), 1.41 (s, 6H); 13C NMR (100 MHz, DMSO-d$_6$) δ 148.9, 142.1, 126.9, 124.7, 71, 45.9, 32.5.

Example 2. N-cyclopentyl-2,4-dimethylthieno[2,3-b: 5,4-c]dipyridin-8-amine (Compound 1)

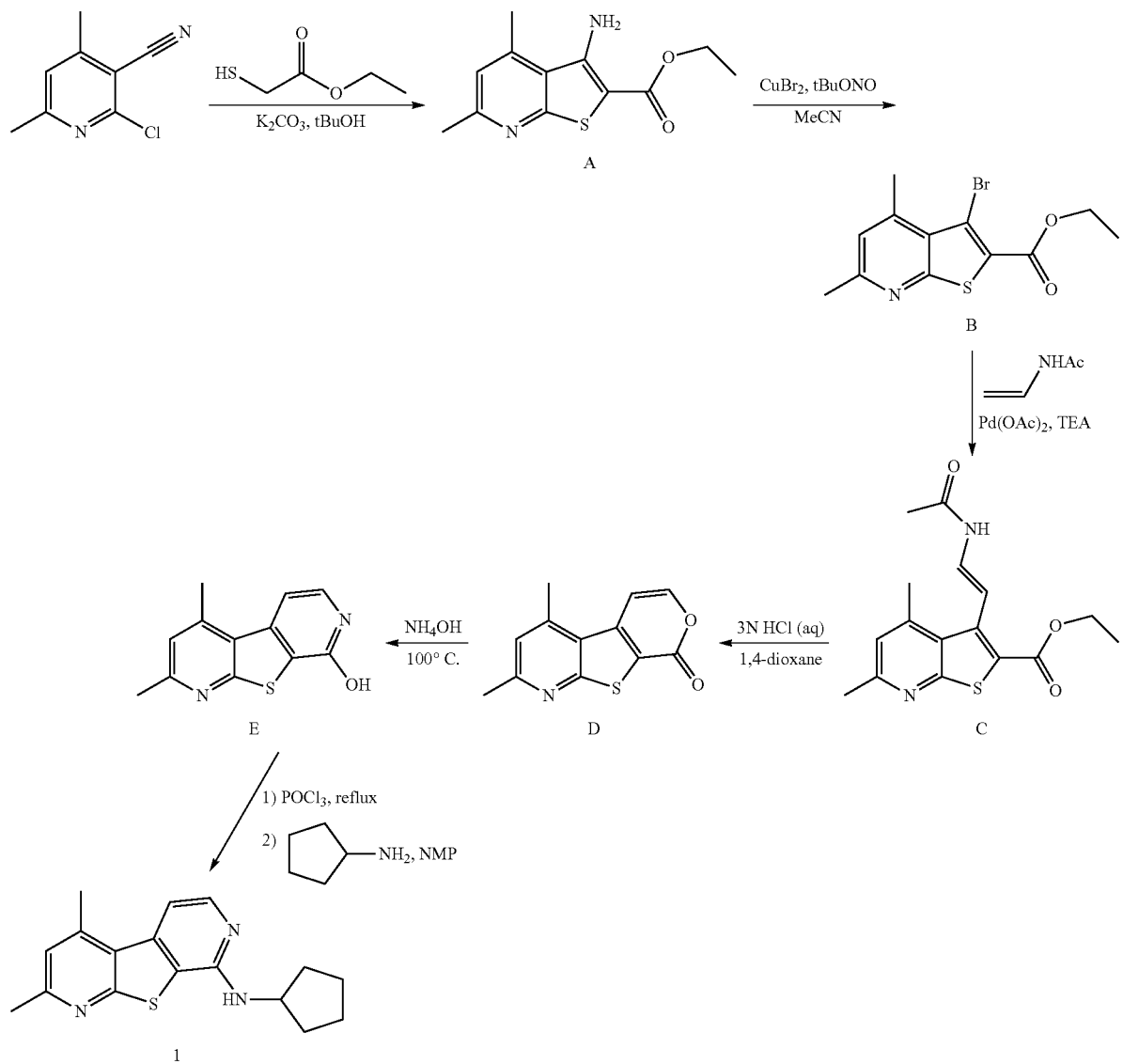

Ethyl 3-amino-4,6-dimethylthieno[2,3-b]pyridine-2-carboxylate (A)

To a 250 mL round bottom flask equipped with a magnetic stir bar were combined 2-chloro-4,6-dimethyl-3-pyridinecarbonitrile (1 g, 6.00 mmol) and ethyl thioglycolate (0.73 mL, 6.59 mmol), followed by tert-butanol (40 mL) and potassium carbonate (1.67 g, 12.0 mmol) at 23° C. The reaction stirred 12 hr. LCMS showed formation of open chain adduct [M+H]$^+$=251. Ethanol (20 mL) was added and the reaction heated to 78° C. for 2 hours when LCMS showed reaction complete. The reaction was diluted with DCM and saturated NaHCO$_3$. The layers were separated and the aqueous layer was extracted with DCM (3×). The combined organics were dried over MgSO$_4$, filtered, and concentrated to give the title compound (1.47 g, 5.87 mmol, 94% yield) as a brown solid. LCMS (90 sec method): R$_T$=0.698 min, 100% @ 215 and 254 nM, m/z=251.2 [M+H]$^+$.

Ethyl 3-bromo-4,6-dimethylthieno[2,3-b]pyridine-2-carboxylate (B)

To a 250 mL round bottom flask equipped with a metal stir bar were combined compound A (1.0 g, 3.99 mmol) and MeCN (16 mL) at 23° C. A solution of cupric bromide (1.61 g, 7.19 mmol) and tert-butyl nitrite (0.665 mL, 5.59 mmol) in MeCN (10 mL) was slowly added via addition funnel over 20 minutes. After addition, the reaction was stirred at 23° C. for 1.5 hr. The reaction was poured into 500 mL water and vigorously stirred. The suspension was vacuum filtered, and washed with copious amounts of water. The solids were isolated and dried by high vacuum to provide the title compound (0.938 g, 2.99 mmol, 74.7% yield), as a brown solid. LCMS (90 sec method): $R_T$=1.078 min, >90% @ 215 and 254 nM, m/z=315.0 [M+H]$^+$.

Ethyl (E)-3-(2-acetamidovinyl)-4,6-dimethylthieno[2,3-b]pyridine-2-carboxylate (C)

To a 20 mL microwave vial containing a heterogeneous solution of compound B (0.981 g, 1.59 mmol), N-vinylacetamide (1.33 g, 15.6 mmol) and triethylamine (2.07 mL, 15.6 mmol) in DMF (12 mL) was bubbled nitrogen gas. After 5 minutes, palladium acetate (70 mg, 0.312 mmol) and tri(o-tolyl)phosphine (190 mg, 0.625 mmol) were added and the vial was immediately capped and subjected to microwave irradiation for 20 minutes at 130° C. The reaction was diluted with water and extracted with EtOAc (3×). The combined organics were washed with water (4×), brine, dried over MgSO$_4$, filtered, and concentrated. The crude sample was taken up in DCM and purified using NP Biotage ZIP (80G cartridge, 1-10% MeOH/DCM). The desired product was concentrated to give the title compound (0.632 g, 1.98 mmol, 63.5% yield) as a brown oil. LCMS (90 sec method): $R_T$=0.754 min, >95% @ 215 and 254 nM, m/z=319.2 [M+H]$^+$.

2,4-Dimethyl-8H-pyrano[4',3'4,5]thieno[2,3-b]pyridin-8-one (D)

To a 20 mL microwave vial containing compound C (0.632 g, 2.08 mmol) and 1,4-dioxane (10 mL) was added 3N HCl solution (13.8 mL, 41.5 mmol). The vial was capped and subjected to microwave irradiation for 20 minutes at 150° C. The reaction was concentrated. The residue was dissolved in methanol and concentrated (3×) to give the title compound (390 mg, 1.18 mmol, 56.8%) as a brown solid. No further purification was done. LCMS (90 sec method): $R_T$=0.743 min, >70% @215 and 254 nM, m/z=232.2 [M+H]$^+$.

2,4-Dimethylthieno[2,3-b:5,4-c']dipyridin-8-ol (E)

To a 50 mL reinforced pressure vessel containing compound D (390 mg, 1.42 mmol) was added ammonium hydroxide (3.29 mL, 84.3 mmol). The vessel was capped and heated to 100° C. for 1.5 hr. The sample was transferred to a flask using DCM/MeOH and concentrated to dryness (azeotroped with methanol). The crude oil was sonicated in IPA and filtered to give the title compound (161 mg, 0.699 mmol, $^4$1.5%) as a brown solid. LCMS (90 sec method): $R_T$=0.546 min, >95% @ 215 and 254 nM, m/z=231.2 [M+H]$^+$.

8-Chloro-2,4-dimethylthieno[2,3-b:5:4-c']dipyridine

To a 20 mL microwave vial containing compound E (161 mg, 0.699 mmol) was added phosphorous (V) oxychloride (3.71 mL, 39.9 mmol). The vial was capped and subjected to microwave irradiation for 30 minutes at 150° C. The sample was transferred to a flask and concentrated to dryness. The crude solid was basified with neat triethylamine until pH>8. The aqueous suspension was extracted with DCM (3×). The combined organics were passed through a phase separator, rinsed with DCM, and concentrated to give the title compound (169 mg, 0.677 mmol, 37.4%) as a brown solid. LCMS (90 sec method): $R_T$=0.931 min, >98% @ 215 and 254 nM, m/z=249.2 [M+H]$^+$.

N-Cyclopentyl-2,4-dimethylthieno[2,3-b:5,4-c]dipyridin-8-amine (Compound 1)

To a 2 mL microwave vial containing 8-chloro-2,4-dimethylthieno[2,3-b:5:4-c']dipyridine (20.0 mg, 0.080 mmol) were added NMP (0.600 mL), cyclopentylamine (200 uL, 1.95 mmol), and N,N-diisopropylethylamine (140 uL, 0.802 mmol). The vial was capped and subjected to microwave irradiation for 60 minutes at 180° C. The sample was purified by RP Gilson (30×50 mm column, 5-35% MeCN/Water/0.1% TFA, 8 minute run). The desired fractions were basified with saturated NaHCO$_3$ (3 mL), and the MeCN was removed via air concentrator. The aqueous suspension was extracted with DCM (3×). The combined organics were passed through a phase separator and concentrated. The solid was dissolved in 0.5 mL DCM and 0.3 mL HCl in 1,4-dioxane (4M). The solvent was removed via air concentrated to give Compound 1 (6.6 mg, 0.018 mmol, 22.1% yield). LCMS (90 sec method): $R_T$=0.730 min, 100% @ 215 and 254 nM, m/z=298.4 [M+H]$^+$.

The compounds shown in Table 1 were prepared in an analogous manner with the appropriate starting materials.

TABLE 1

| Cpd. No. | Name | Structure | ES-MS [M + 1]$^+$ |
|---|---|---|---|
| 2 | 2,4-dimethyl-8-(pyrrolidin-1-yl)thieno[2,3-b:5,4-c']dipyridine | 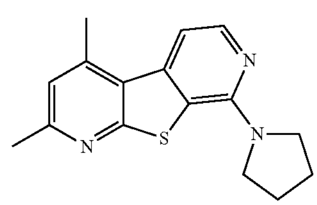 [SMILES: Cc1cc(C)c2c(n1)sc1c(N3CCCC3)nccc12] | 284 |
| 3 | N-cyclobutyl-2,4-dimethylthieno[2,3-b:5,4-c']dipyridin-8-amine dihydrochloride | 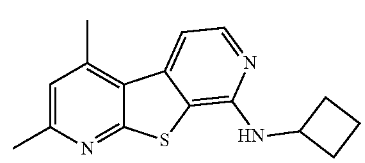 [SMILES: Cc1cc(C)c2c(n1)sc1c(NC3CCC3)nccc12] | 284 |

TABLE 1-continued

| Cpd. No. | Name | Structure | ES-MS [M + 1]+ |
|---|---|---|---|
| 4 | N,N,2,4-tetramethylthieno[2,3-b:5,4-c']dipyridin-8-amine | 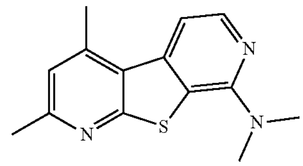 | 258 |
| 24 | 2,4-dimethyl-N-(1-(5-(trifluoromethyl)pyrimidin-2-yl)azetidin-3-yl)thieno[2,3-b:5,4-c']dipyridin-8-amine | 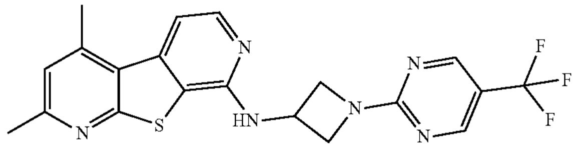 [SMILES: Cc1cc(C)c2c(n1)sc1c(NC3CN(c4ncc(C(F)(F)F)cn4)C3)nccc12] | 431.3 |
| 25 | N-(3-fluoro-4-methoxybenzyl)-2,4-dimethylthieno[2,3-b:5,4-c']dipyridin-8-amine | 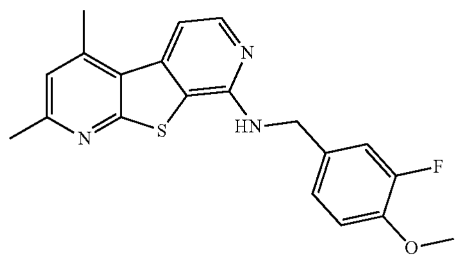 | 368.3 |
| 26 | 2-(4-(((2,4-dimethylthieno[2,3-b:5,4-c']dipyridin-8-yl)amino)methyl)phenyl)propan-2-ol | 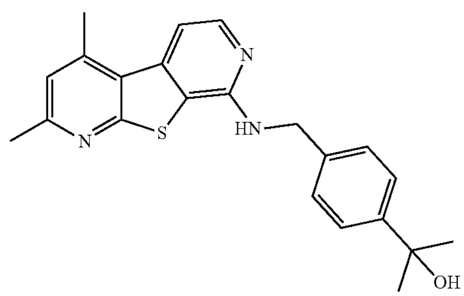 [SMILES: Cc1cc(C)c2c(n1)sc1c(NCc3ccc(C(C)(C)O)cc3)nccc12] | 378 |
| 27 | 2-(4-(((2,4-dimethylthieno[2,3-b:5,4-c']dipyridin-8-yl)amino)methyl)-3-fluorophenyl)propan-2-ol | 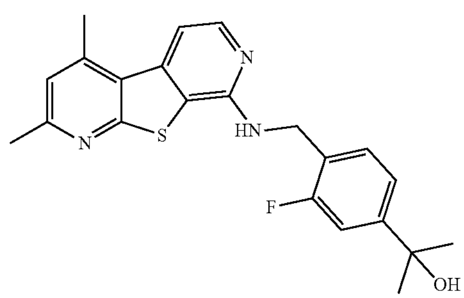 [SMILES: Cc1cc(C)c2c(n1)sc1c(NCc3ccc(C(C)(C)O)cc3F)nccc12] | 396 |

Example 3. N-Cyclopentyl-3,4-dimethyl-pyrido[4',3':4,5]thieno[2,3-c]pyridazin-8-amine (Compound 5)

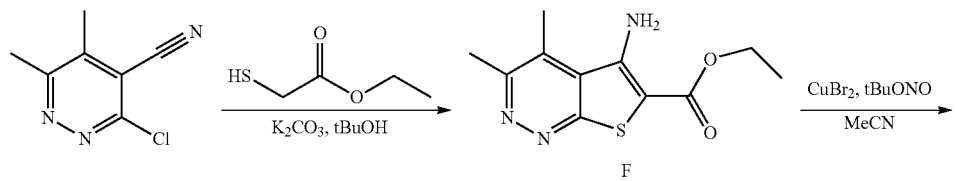

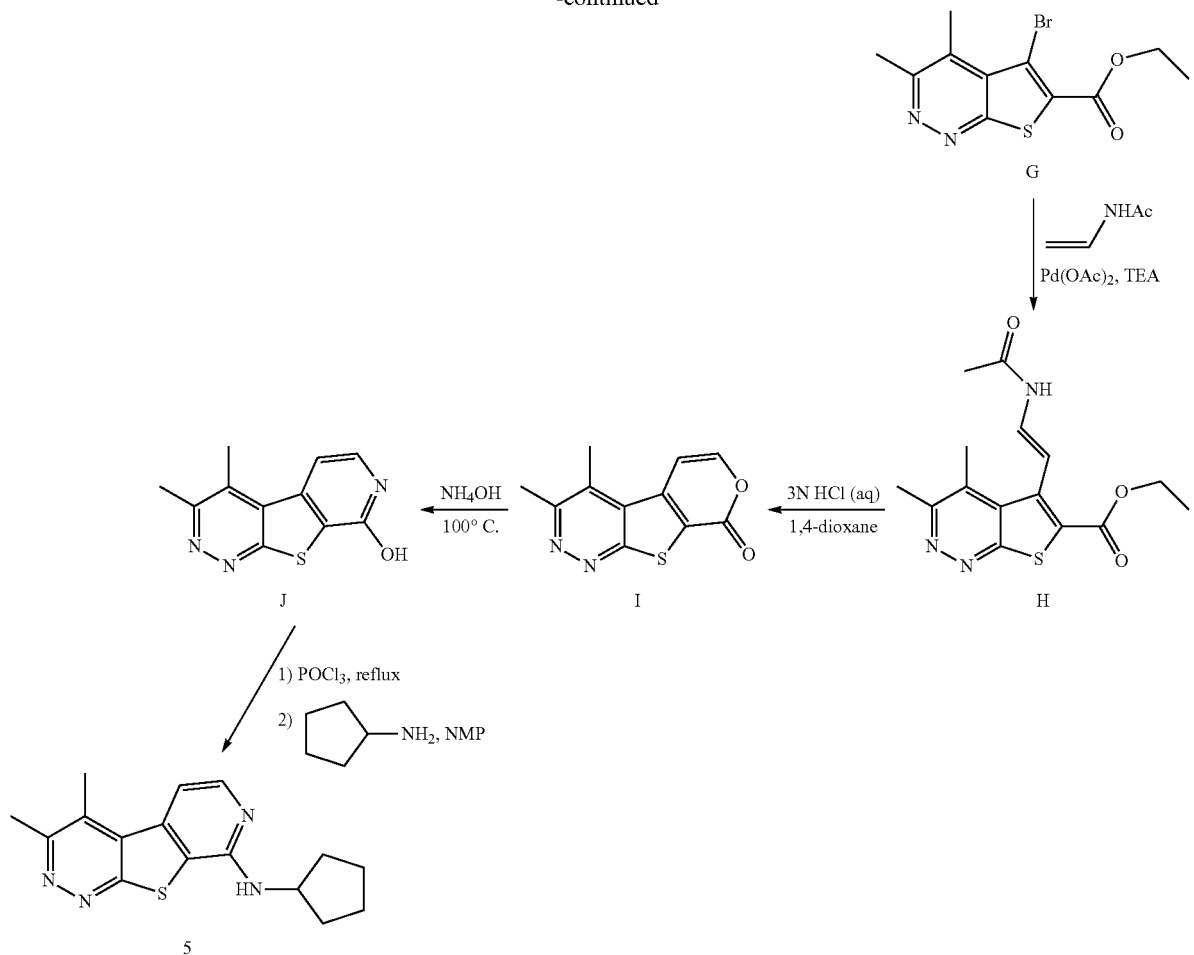

Ethyl 5-amino-3,4-dimethylthieno[2,3-c]pyridazine-6-carboxylate (F)

To a 250 mL round bottom equipped with a magnetic stir bar were combined 3-chloro-5,6-dimethylpyridazine-4-carbonitrile (1.g, 5.97 mmol) and ethyl thioglycolate (0.72 mL, 6.56 mmol), followed by tert-butanol (40 mL) and potassium carbonate (1.67 g, 11.93 mmol) at 23° C. The reaction stirred 12 hr. LCMS showed formation of open chain adduct [M+H]$^+$=252. Ethanol (20 mL) was added and the reaction heated to 78° C. for 2 hours when LCMS showed the reaction was complete. The reaction was diluted with DCM and saturated NaHCO$_3$. The layers were separated and the aqueous was extracted with DCM (3×). The combined organics were dried over MgSO$_4$, filtered, and concentrated to give the title compound (1.47 g, 5.85 mmol, 98.0% yield) as a brown solid. LCMS (90 sec method): R$_T$=0.666 min, 100% @ 215 and 254 nM, m/z=252.2 [M+H]$^+$.

Ethyl 5-bromo-3,4-dimethylthieno[2,3-c]pyridazine-6-carboxylate (G)

To a 250 mL round bottom flask equipped with a metal stir bar were combined compound F (3.8 g, 15.12 mmol) and MeCN (25 mL) at 23° C. A solution of cupric bromide (1.69 g, 7.56 mmol) and tert-butyl nitrite (2.53 mL, 21.17 mmol) in MeCN (20 mL) was slowly added via addition funnel over 20 minutes. After addition, the reaction stirred at 23° C. for 1.5 hr. The reaction was poured into 500 mL water and vigorously stirred. The suspension was vacuum filtered, and washed with water (~1000 mL). The solids were isolated and dried by high vacuum to give the title compound (3.12 g, 9.90 mmol, 65.5% yield), as a brown solid. LCMS (90 sec method): R$_T$=0.855 min, >90% @ 215 and 254 nM, m/z=316.0 [M+H]$^+$.

Ethyl (E)-5-(2-acetamidovinyl)-3,4-dimethylthieno[2,3-c]pyridazine-6-carboxylate (H)

To a 20 mL microwave vial containing a heterogeneous solution of compound G (0.50 g, 1.59 mmol), N-vinylacetamide (0.68 g, 7.93 mmol) and triethylamine (1.05 mL, 7.93 mol) in DMF (8 mL) was bubbled nitrogen gas. After 2 minutes of nitrogen exposure, palladium acetate (36 mg, 0.159 mmol) and tri(o-tolyl)phosphine (97 mg, 0.317 mmol) were added and the vial was immediately capped and subjected to microwave irradiation for 20 minutes at 130° C. The reaction was diluted with water and extracted with EtOAc (3×). The combined organics were washed with water (4×), brine, dried over MgSO$_4$, filtered, and concentrated. The crude sample was taken up in DCM and purified using NP Biotage ZIP (80G cartridge, 1-10% MeOH/DCM). The desired product was concentrated to give the title compound (0.73 g, 2.89 mmol, 48.5% yield) as a brown oil. LCMS (90 sec method): R$_T$=0.651 min, >90% @ 215 and 254 nM, m/z=320.2 [M+H]$^+$.

3,4-Dimethyl-8H-pyrano[4',3':4,5]thieno[2,3-c]pyridazin-8-one (I)

To a 20 mL microwave vial containing compound H (0.325 g, 1.02 mmol) and 1,4-dioxane (3 mL) was added 3N HCl solution (6.8 mL, 20.3 mmol). The vial was capped and subjected to microwave irradiation for 20 minutes at 150° C. The reaction was concentrated and azeotroped with methanol (3x) to give the title compound (82.5 mg, 0.35 mmol) as a brown solid. No further purification was done. LCMS (90 sec method): R$_T$=0.513 min, >70% @ 215 and 254 nM, m/z=233.2 [M+H]$^+$.

3,4-Dimethylpyrido[4',3':4,5]thieno[2,3-c]pyridazin-8-ol (J)

To a 50 mL reinforced pressure vessel containing compound I (330 mg, 1.42 mmol) was added ammonium hydroxide (2.77 mL, 71.0 mmol, 28-30% NH$_3$ basis). The vessel was capped and heated to 100° C. for 1.5 hr. The sample was transferred to a flask using DCM/MeOH and concentrated to dryness (azeotroped with methanol, 2×100 mL). The crude oil was sonicated in IPA and filtered to give the title compound (235 mg, 1.02 mmol) as a brown solid. LCMS (90 sec method): R$_T$=0.300 min, >95% @ 215 and 254 nM, m/z=232.3 [M+H].

8-Chloro-3,4-dimethylpyrido[4',3':4,5]thieno[2,3-c]pyridazine

To a 20 mL microwave vial containing compound J (249 mg, 1.08 mmol) was added phosphorous (V) oxychloride (10.0 mL, 108 mmol). The vial was capped and subjected to microwave irradiation for 30 minutes at 150° C. The sample was transferred to a flask and concentrated to dryness. The crude solid was basified with neat triethylamine until pH>8. The aqueous suspension was extracted with DCM (3x). The combined organics were passed through a phase separator, rinsed with DCM, and concentrated to give the title compound (169 mg, 0.677 mmol) as a brown solid. LCMS (90 sec method): R$_T$=0.750 min, >98% @ 215 and 254 nM, m/z=250.2 [M+H]$^+$.

N-Cyclopentyl-3,4-dimethyl-pyrido[4',3':4,5]thieno[2,3-c]pyridazin-8-amine Hydrochloride (Compound 5)

To a 2 mL microwave vial containing 8-chloro-3,4-dimethylpyrido[4',3':4,5]thieno[2,3-c]pyridazine (15.0 mg, 0.060 mmol) were added NMP (0.600 mL), cyclopentylamine (236.25 uL, 2.4 mmol), and N,N-diisopropylethylamine (209.25 uL, 1.2 mmol). The vial was capped and subjected to microwave irradiation for 60 minutes at 180° C. The sample was purified by RP Gilson (30×50 mm column, 5-35% MeCN/Water/0.1% TFA, 8 minute run). The desired fractions were basified with saturated NaHCO$_3$ (3 mL), and the MeCN was removed via air concentrator. The aqueous suspension was extracted with DCM (3x). The combined organics were passed through a phase separator and concentrated to give the title compound (4 mg, 0.012 mmol, 19.9% yield). LCMS (90 sec method): R$_T$=0.637 min, 100% @215 and 254 nM, m/z=299.2 [M+H]$^+$. HRMS=298.1253.

The compounds shown in Table 2 were prepared in an analogous manner with the appropriate starting materials.

TABLE 2

| Cpd. No. | Name | Structure | ES-MS [M + 1]$^+$ |
|---|---|---|---|
| 6 | 3,4-dimethyl-8-pyrrolidin-1-yl-pyrido[4',3':4,5]thieno[2,3-c]pyridazine hydrochloride | 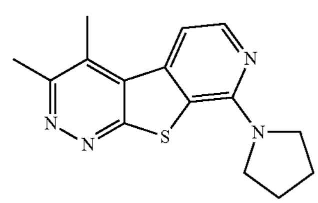 [SMILES: Cc1nnc2sc3c(N4CCCC4)nccc3c2c1C] | 285 |
| 7 | N-cyclobutyl-3,4-dimethyl-pyrido[4',3':4,5]thieno[2,3-c]pyridazin-8-amine hydrochloride | 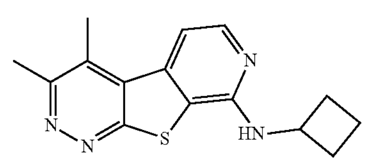 [SMILES: Cc1nnc2sc3c(NC4CCC4)nccc3c2c1C] | 285 |
| 8 | N-cyclopropyl-3,4-dimethyl-pyrido[4',3':4,5]thieno[2,3-c]pyridazin-8-amine hydrochloride | 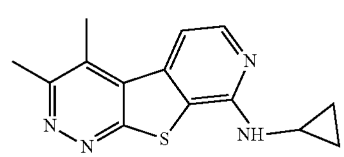 [SMILES: Cc1nnc2sc3c(NC4CC4)nccc3c2c1C] | 271 |

TABLE 2-continued

| Cpd. No. | Name | Structure | ES-MS [M + 1]+ |
|---|---|---|---|
| 9 | N-[(4-methoxyphenyl)methyl]-3,4-dimethyl-pyrido[4',3':4,5]thieno[2,3-c]pyridazin-8-amine hydrochloride | 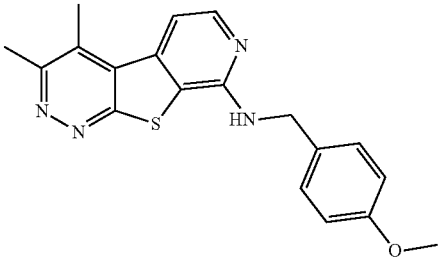 | 351 |
| 10 | 3,4-dimethyl-N-[1-[5-(trifluoromethyl)pyrimidin-2-yl]azetidin-3-yl]pyrido[4',3':4,5]thieno[2,3-c]pyridazin-8-amine hydrochloride | 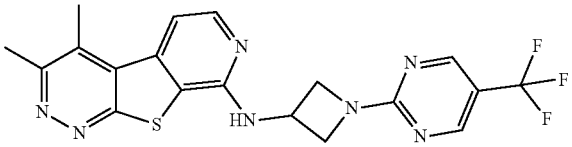 [SMILES: Cc1nnc2sc3c(NC4CN(c5ncc(C(F)(F)F)cn5)C4)nccc3c2c1C] | 432 |
| 11 | 3,4-dimethyl-N-[[4-(trifluoromethoxy)phenyl]methyl]pyrido[4',3':4,5]thieno[2,3-c]pyridazin-8-amine hydrochloride | 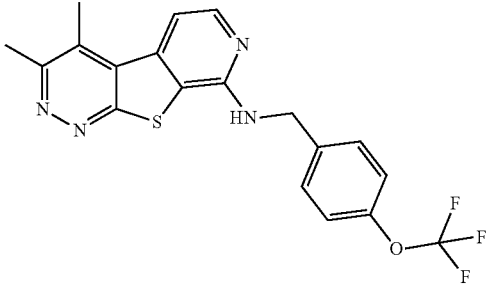 [SMILES: Cc1nnc2sc3c(NCc4ccc(OC(F)(F)F)cc4)nccc3c2c1C] | 405 |
| 12 | N-[1-(5-fluoropyrimidin-2-yl)azetidin-3-yl]-3,4-dimethyl-pyrido[4',3':4,5]thieno[2,3-c]pyridazin-8-amine hydrochloride | 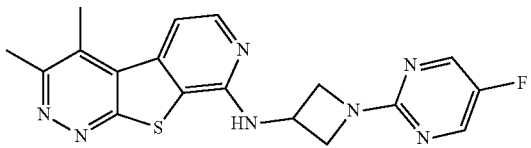 [SMILES: Cc1nnc2sc3c(NC4CN(c5ncc(F)cn5)C4)nccc3c2c1C] | 382 |
| 13 | [4-[[(3,4-dimethylpyrido[4',3':4,5]thieno[2,3-c]pyridazin-8-yl)amino]methyl]phenyl]-morpholino-methanone | 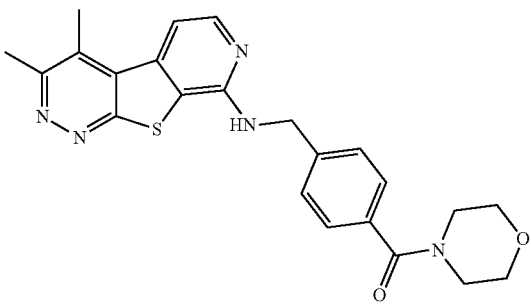 [SMILES: Cc1nnc2sc3c(NCc4ccc(C(=O)N5CCOCC5)cc4)nccc3c2c1C] | 434 |
| 14 | N-[(3-fluoro-4-methoxy-phenyl)methyl]-3,4-dimethylpyrido[4',3':4,5]thieno[2,3-c]pyridazin-8-amine hydrochloride | 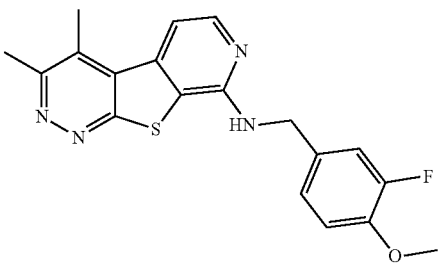 | 369 |

TABLE 2-continued

| Cpd. No. | Name | Structure | ES-MS [M + 1]+ |
|---|---|---|---|
| 15 | 2-[4-[[(3,4-dimethylpyrido[4',3':4,5]thieno[2,3-c]pyridazin-8-yl)amino]lmethyl]phenyl]propan-2-ol | 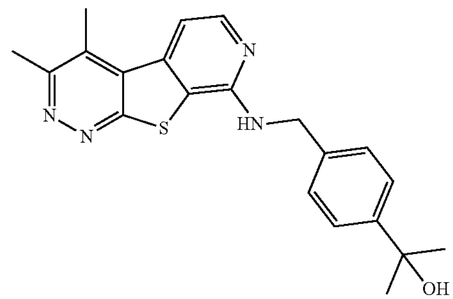 [SMILES: Cc1nnc2sc3c(NCc4ccc(C(C)(C)O)cc4)nccc3c2c1C] | 379 |
| 16 | N-[(3,4-difluorophenyl)methyl]-3,4-dimethyl-pyrido[4',3':4,5]thieno[2,3-c]pyridazin-8-amine hydrochloride | 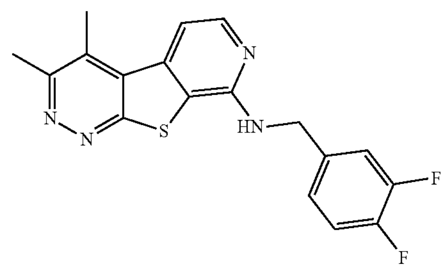 [SMILES: Cc1nnc2sc3c(NCc4ccc(F)c(F)c4)nccc3c2c1C] | 357 |
| 17 | N-[[3-fluoro-4-(trifluoromethyl)phenyl]methyl]-3,4-dimethyl-pyrido[4',3':4,5]thieno[2,3-c]pyridazin-8-amine hydrochloride | 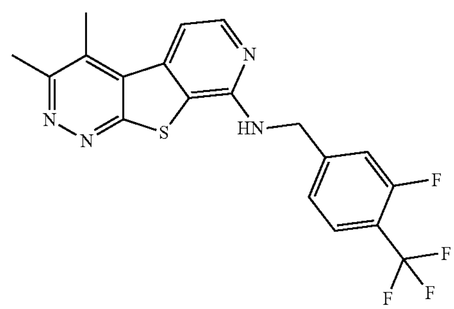 [SMILES: Cc1nnc2sc3c(NCc4ccc(C(F)(F)F)c(F)c4)nccc3c2c1C] | 407 |
| 18 | N-[[4-(cyclopropylmethoxy)-3-fluoro-phenyl]methyl]-3,4-dimethyl-pyrido[4',3':4,5]thieno[2,3-c]pyridazin-8-amine hydrochloride | 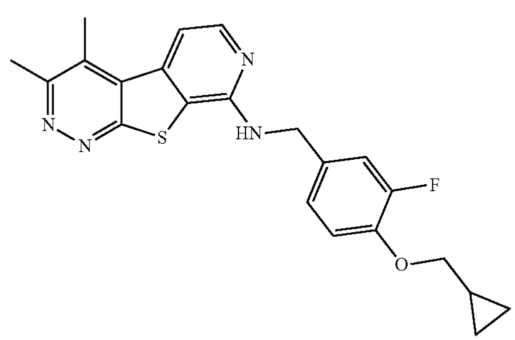 [SMILES: Cc1nnc2sc3c(NCc4ccc(OCC5CC5)c(F)c4)nccc3c2c1C] | 409 |
| 19 | N-[1-(3,4-difluorophenyl)azetidin-3-yl]-3,4-dimethyl-pyrido[4',3':4,5]thieno[2,3-c]pyridazin-8-amine hydrochloride | 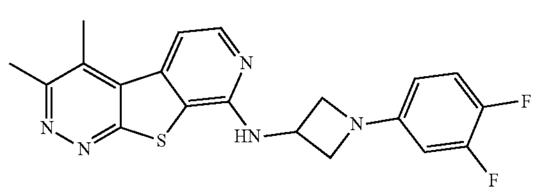 [SMILES: Cc1nnc2sc3c(NC4CN(c5ccc(F)c(F)c5)C4)nccc3c2c1C] | 398 |

TABLE 2-continued

| Cpd. No. | Name | Structure | ES-MS [M + 1]+ |
|---|---|---|---|
| 20 | 2-[4-[[(3,4-dimethylpyrido[4',3':4,5]thieno[2,3-c]pyridazin-8-yl)amino]methyl]-2-fluoro-phenyl]propan-2-ol | 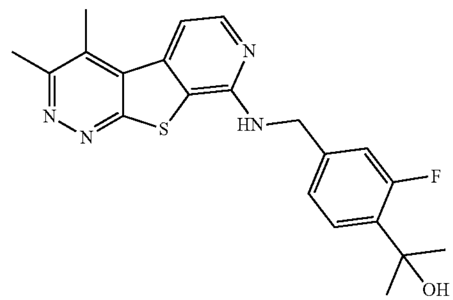 [SMILES: Cc1nnc2sc3c(NCc4ccc(C(C)(C)O)c(F)c4)nccc3c2c1C] | 397 |
| 21 | 2-[4-[[(3,4-dimethylpyrido[4',3':4,5]thieno[2,3-c]pyridazin-8-yl)amino]methyl]-3-fluoro-phenyl]propan-2-ol | 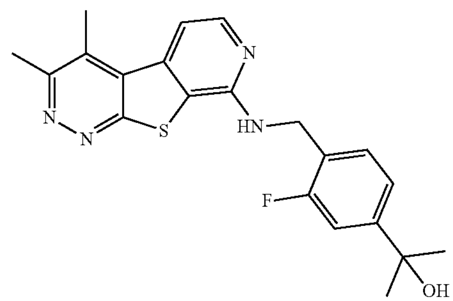 [SMILES: Cc1nnc2sc3c(NCc4ccc(C(C)(C)O)cc4F)nccc3c2c1C] | 397 |
| 22 | 6-[3-[(3,4-dimethylpyrido[4',3':4,5]thieno[2,3-c]pyridazin-8-yl)amino]azetidin-1-yl]pyridine-3-carbonitrile | 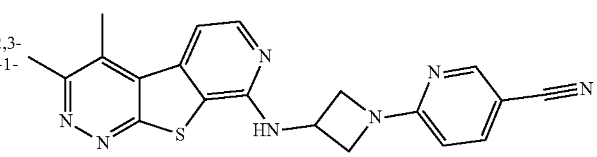 | 388 |

Example 4. 5-Chloro-3,4-dimethyl-8-pyrrolidin-1-yl-pyrido[4',3':4,5]thieno[2,3-c]pyridazine Hydrochloride (Compound 23)

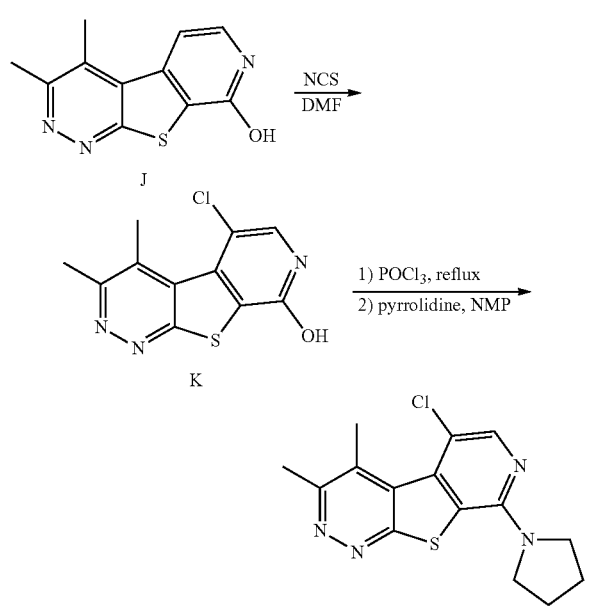

5-Chloro-3,4-dimethylpyrido[4',3':4,5]thieno[2,3-c]pyridazin-8-ol (K)

To a vial equipped with a magnetic stir bar was added purified 3,4-dimethylpyrido[4',3':4,5]thieno[2,3-c]pyridazin-8-ol (Compound J, see Example 2) (40 mg, 0.17 mmol) dissolved in DMF (1.7 mL). Next, N-chlorosuccinimide (23.1 mg, 0.17000 mmol) was added to the reaction and the reaction was stirred for 18 hr. LCMS confirmed product. To the reaction was added 15 mL of 5% aqueous LiCl and extracted with $CHCl_3$/IPA (4:1) (5×5 mL). The organic extracts where passed through a phase separator and concentrated to afford 5-chloro-3,4-dimethyl-pyrido[4,5]thieno[1,2-c]pyridazin-8-ol in quantitative yield. LCMS (90 sec method): $R_T$=0.616 min, >86% @ 215 and 254 nM, m/z=266.4 [M+H]+.

5,8-Dichloro-3,4-dimethylpyrido[4',3':4,5]thieno[2,3-c]pyridazine

Into a microwave vial were combined compound K (46 mg, 0.17 mmol), DCE (0.16 mL), and phosphorous (V) oxychloride (0.81 mL, 8.65 mmol). The vial was capped and subjected to microwave irradiation for 50 minutes at 150° C. LCMS showed reaction was incomplete (33% starting material; 47% desired product). To drive the reaction forward, triethylamine (36.17 uL, 0.26 mmol) was added to the vial. The vial was capped and heated for 5.5 hr at 100° C. on benchtop. The reaction was concentrated to dryness and basified with neat triethylamine until pH>8. The basic solution was then extracted with DCM (3×). The combined organics were passed through a phase separator, rinsed with DCM, and concentrated to dryness. Crude product was purified using Teledyne ISCO Combi-Flash system (liquid loading in DCM, 12G column, 0-5% MeOH/DCM, 12 minute run). The desired peak was concentrated to give 5,8-dichloro-3,4-dimethylpyrido[4',3':4,5]thieno[2,3-c] pyridazine (22.2 mg, 0.066 mmol, 38.4% yield) as a dark brown solid. LCMS (90 sec method): $R_T$=0.834 min, >89% @ 254 nM, m/z=284.0 [M+H]$^+$.

5-Chloro-3,4-dimethyl-8-(pyrrolidin-1-yl)pyrido[4', 3':4,5]thieno[2,3-c]pyridazine (Compound 23)

To a microwave vial containing 5,8-dichloro-3,4-dimethylpyrido[4',3':4,5]thieno[2,3-c]pyridazine (11.mg, 0.030 mmol) were added DMF (0.50 mL), pyrrolidine (13.51 uL, 0.16 mmol), and N,N-diisopropylethylamine (17.19 uL, 0.10 mmol). The vial was capped and the sample was subjected to microwave irradiation for 30 minutes at 150° C. The reaction was determined to be complete by LCMS. The sample was transferred directly to the RP Gilson for purification (30×100 mm column, 20-60% MeCN/Water/0.1% TFA, 10 minute run). The desired fractions were concentrated to remove ACN to give an orange aqueous solution. The aqueous solution was basified with saturated NaHCO$_3$ then extracted with CHCl$_3$/IPA (4:1). The combined organics were passed through a phase separator and concentrated to give 5.9 mg of desired product (bright yellow solid).

The yellow solid was dissolved in DCM and 4M solution in 1,4-dioxane HCl (0.10 mL, 0.40 mmol) was added (turned dark orange/red). The suspension was concentrated to afford the title compound (7.4 mg, 0.021 mmol, 63.3% yield) as a brown-orange solid. LCMS (90 sec method): $R_T$=0.803; 100% @ 215 and 254 nM, m/z=319.2 [M+H]$^+$.

Example 5. 3-Chloro-N-(4-methoxybenzyl)-2,4-dimethylthieno[2,3-b:5,4-c']dipyridin-8-amine (Compound 28)

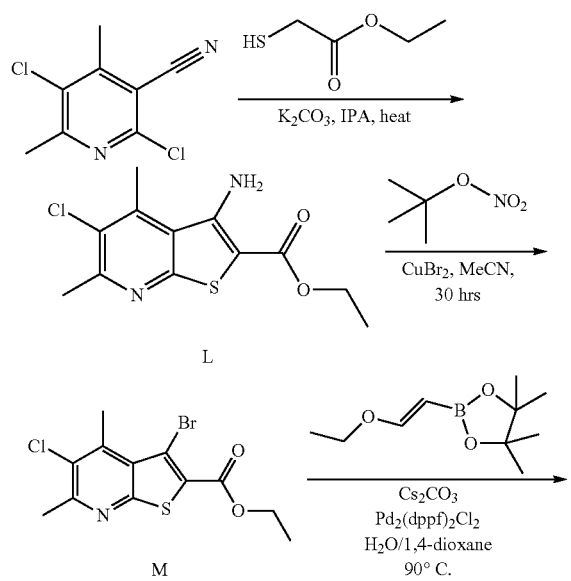

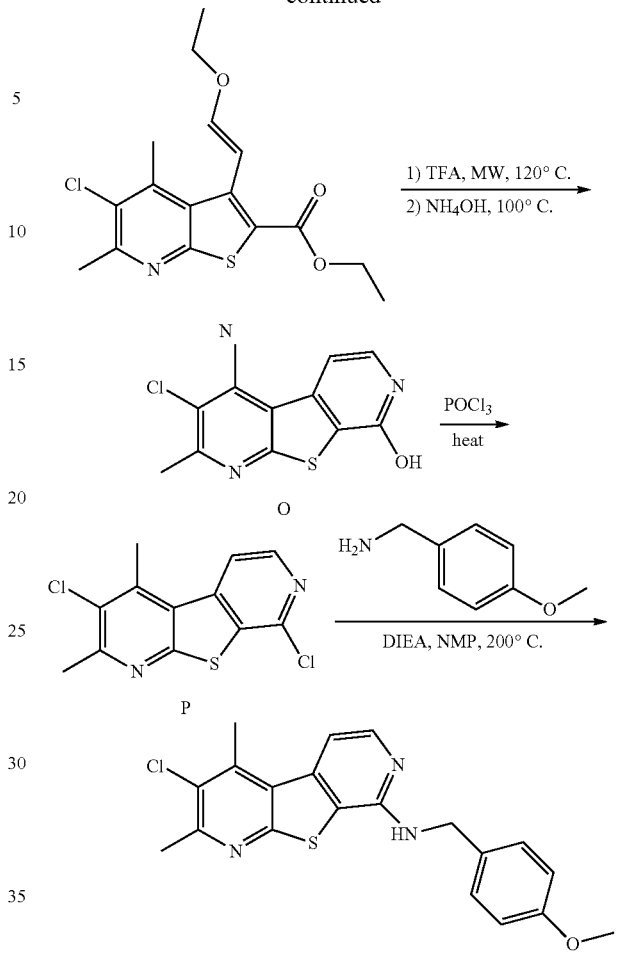

Ethyl 3-amino-5-chloro-4,6-dimethylthieno[2,3-b] pyridine-2-carboxylate (L)

2,5-Dichloro-4,6-dimethylnicotinonitrile (3 g, 14.92 mmol, 1 eq.), ethyl thioglycolate (1.97 mL, 17.91 mmol, 1.2 eq.), potassium carbonate (4.18 g, 29.84 mmol, 2 eq.) and isopropyl alcohol (21 mL) were added equally to three microwave vials. The vials were capped and heated in a microwave reactor at 150° C. for 30 minutes. The reaction was diluted with water to become heterogeneous and viscous. After stirring for 20 minutes at room temperature, the solids were filtered and washed three times with water to afford 4.12 g (97%) of the title compound which was used without further purification. $^1$H NMR (400 MHz, CDCl$_3$) δ 6.17 (s, 2H), 4.35 (q, J=7.08, 7.12 Hz, 2H), 2.87 (s, 3H), 2.72 (s, 3H), 1.39 (t, J=7.12 Hz, 3H); ES-MS [M+1]$^+$: 285.2.

Ethyl 3-bromo-5-chloro-4,6-dimethylthieno[2,3-b] pyridine-2-carboxylate (M)

To a solution of cupric bromide (0.44 mL, 9.48 mmol, 1.8 eq.) and tert-butyl nitrite (0.88 mL, 7.37 mmol, 1.4 eq.) in acetonitrile (40 mL) was slowly added compound L (1.5 g, 5.27 mmol, 1 eq.) over two minutes. After 3 hours, the reaction was diluted with 100 mL of water. A light blue precipitate formed and was collected by vacuum filtration.

The solid was washed three times with water and dried to afford 1.66 g (91%) of the title compound. 1H NMR (400 MHz, CDCl$_3$) δ 4.43 (q, J=6.88, 7.04 Hz, 2H), 3.10 (s, 3H), 2.75 (s, 3H), 1.43 (t, J=7.0 Hz, 3H); ES-MS [M+1]$^+$:350.2.

Ethyl (E)-5-chloro-3-(2-ethoxyvinyl)-4,6-dimethyl-thieno[2,3-b]pyridine-2-carboxylate (N)

Compound M (1.5 g, 4.48 mmol, 1 eq.), (E)-1-ethoxyethene-2-boronic acid pinacol ester (1.05 mL, 4.9 mmol, 1.1 eq.), Pd$_2$(dppf)$_2$Cl$_2$— CH$_2$Cl$_2$ (164 mg, 0.22 mmol, 0.05 eq.), cesium carbonate (4.4 g, 13.45 mmol, 3 eq.), water (2 mL) and 1,4-dioxane (20 mL) were added to a vial (40 mL). After bubbling nitrogen through the solution for 5 minutes, the vial was capped and heated to 90° C. for 6 hours. The reaction was filtered over a pad of Celite, washed with DCM/EtOAc (3×) and concentrated. The crude product was purified by flash chromatography on silica gel using 0-70% ethyl acetate/hexanes to provide the title compound (1.2 g, 82% yield). ES-MS [M+1]$^+$: 326.3.

3-Chloro-2,4-dimethylthieno[2,3-b:5,4-c']dipyridin-8-ol (O)

Divided equally between two 20 mL microwave vials, a solution of compound N (1.2 g, 3.68 mmol, 1.0 eq) in trifluoroacetic acid (13 mL) was heated in a Biotage microwave at 120° C. for 30 minutes. The reaction was followed by LCMS and subjected to further microwave irradiation until reaction was complete. The solution was concentrated under vacuo and azeotroped with toluene (2×100 mL). The residue was combined in a reinforced pressure vessel with NH$_4$OH (10.5 mL) and the vessel was sealed and heated to 100° C. for 18 hr. The mixture was concentrated then dried in vacuo and taken forward without further purification. ES-MS [M+1]$^+$: 265.0.

3,8-Dichloro-2,4-dimethylthieno[2,3-b:5,4-c']dipyridine (P)

Phosphorus oxychloride (9 mL, 97.3 mmol) was added to compound O and the mixture was subjected to microwave reactor at 120° C. for 30 minutes. The solution was concentrated and the residue suspended in DCM (20 mL). To the mixture was added Et$_3$N (3.8 mL, 27 mmol). The mixture was filtered and the filtrate was concentrated. The crude residue was purified by flash chromatography on silica gel (MeOH/DCM/NH$_4$OH (10:89:1) solution with DCM, 0-50%) to provide the title compound (0.24 g, 23% yield over 3 steps). ES-MS [M+1]$^+$: 285.8

3-Chloro-N-(4-methoxybenzyl)-2,4-dimethylthieno[2,3-b:5,4-c]dipyridin-8-amine (Compound 28)

Compound P (10 mg, 0.04 mmol, 1 eq.), 4-methoxybenzylamine (7.5 mg, 0.05 mmol, 1.5 eq.), DIEA (0.025 mL, 0.14 mmol, 4.0 eq.) and NMP (1 mL) were added to a microwave vial. The vial was capped and heated in a microwave reactor to 180° C. for 3 hours. The residue was purified by reverse phase HPLC (5-95% acetonitrile:water with 0.1% TFA). The desired fractions were collected and neutralized with a saturated solution of NaHCO$_3$. The mixture was extracted with CHCl$_3$/IPA (3:1, 3×). The collected organic layers were concentrated to afford 6 mg (45%) of the title compound. $^1$H NMR (400 MHz, CDCl$_3$) δ 8.17 (d, J=5.76 Hz, 1H), 7.41 (d, J=5.76 Hz, 1H), 7.3 (d, J=8.64 Hz, 2H), 6.83 (d, J=8.64 Hz, 2H), 4.70 (d, J=5.32 Hz, 2H), 4.51 (t, J=5.24 Hz, 1H), 3.74 (s, 3H) 2.88 (s, 3H), 2.70 (s, 3H); ES-MS [M+1]$^+$: 383.9.

The compounds shown in Table 3 were prepared in an analogous manner with the appropriate starting materials.

TABLE 3

| Cpd. No. | Name | Structure | ES-MS [M + 1]$^+$ |
|---|---|---|---|
| 29 | 2-(4-(((3-chloro-2,4-dimethylthieno[2,3-b:5,4-c']dipyridin-8-yl)amino)methyl)phenyl)propan-2-ol | 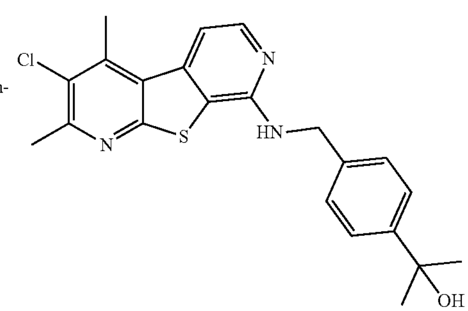 | 412.3 |
| 30 | 3-chloro-2,4-dimethyl-8-(pyrrolidin-1-yl)thieno[2,3-b:5,4-c']dipyridine | 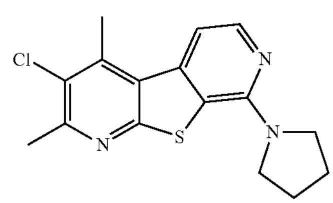 [SMILES: Cc1nc2sc3c(N4CCCC4)nccc3c2c(C)c1Cl] | 318 |

TABLE 3-continued
| Cpd. No. | Name | Structure | ES-MS [M + 1]+ |
|---|---|---|---|
| 31 | 2-(4-(((3-chloro-2,4-dimethylthieno[2,3-b:5,4-c']dipyridin-8-yl)amino)methyl)-2-fluorophenyl)propan-2-ol | 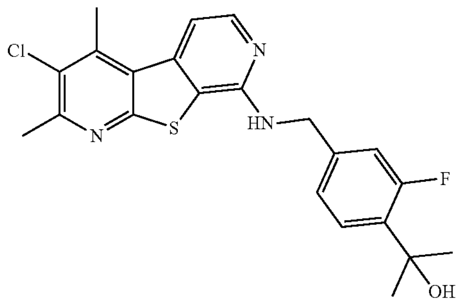 [SMILES: Cc1nc2sc3c(NCc4ccc(C(C)(C)O)c(F)c4)nccc3c2c(C)c1Cl] | 429.9 |
Example 6. 3-chloro-N-(4-methoxybenzyl)-4-methylpyrido[4',3':4,5]thieno[2,3-c]pyridazin-8-amine (Compound 32)
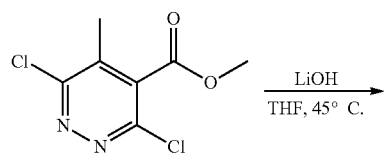
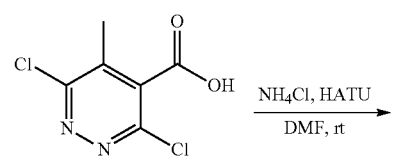
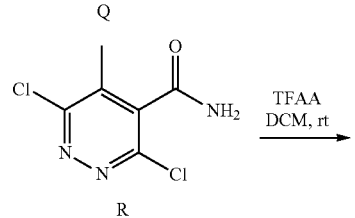
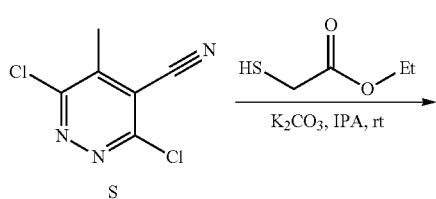
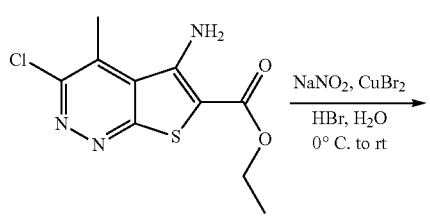
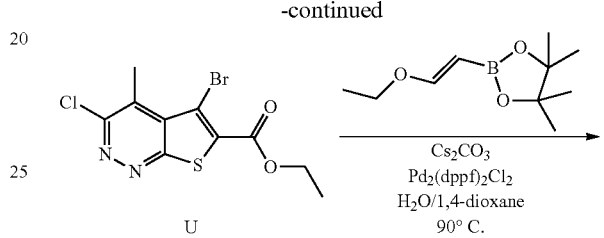
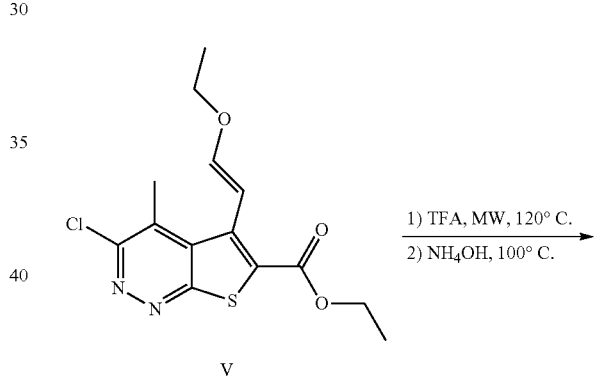
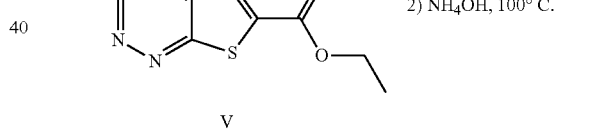
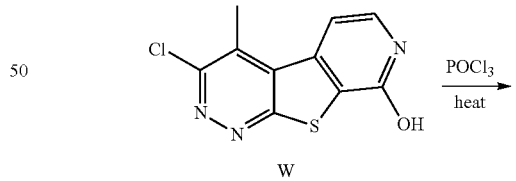
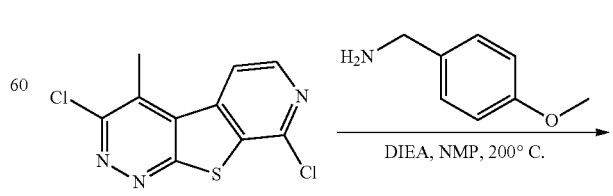

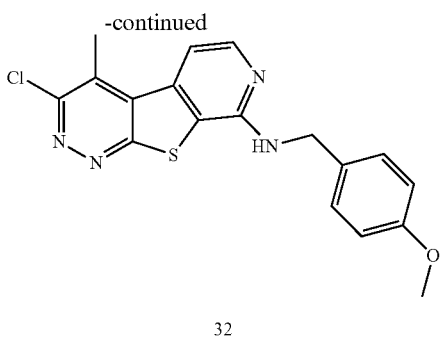

32

3,6-Dichloro-5-methylpyridazine-4-carboxylic Acid (Q)

In a 100 mL round-bottom flask fitted with a magnetic stir bar and a septum was added methyl 3,6-dichloro-5-methylpyridazine-4-carboxylate (8.5 g, 38.45 mmol), lithium hydroxide (40.4 mL, 40.4 mmol) and THF (38.5 mL). The reaction was heated to 45° C. for 12 h. The reaction was cooled and checked by LCMS for complete consumption of starting material. The biphasic mixture was then diluted with EtOAc (25 ml) and acidified to pH=2 with 1N HCl. The aqueous mixture was extracted with EtOAc (3×25 mL). The organic fractions were combined and washed with brine, dried over MgSO$_4$, filtered and concentrated to provide the title compound. It was used without further purification. LCMS: RT=0.224 min, M+H=207.2, >96% at 215 and 254 nm.

3,6-Dichloro-5-methylpyridazine-4-carboxamide (R)

In a 100 mL round-bottom flask fitted with a magnetic stir bar and a septum was added compound Q (7.9 g, 38.5 mmol), HATU (17.6 g, 46.2 mmol), ammonium chloride (6.2 g, 115.4 mmol) and DMF (75 mL). The suspension was stirred for 10 minutes and DIEA (33.5 mL, 192.3 mmol) was added and the mixture turned dark orange. The reaction was stirred at 25° C. for 2 h or until complete conversion was seen by LCMS. The reaction was diluted with water and extracted with EtOAc (100 mL). The aqueous phase was further extracted with EtOAc (2×25 ml). The combined organic fractions were washed with brine, separated and dried over MgSO$_4$, filtered and concentrated. The residue was used without further purification. LCMS: RT=0.368 min, M+H=206.3.

3,6-Dichloro-5-methylpyridazine-4-carbonitrile (S)

In a 200 mL round-bottom flask fitted with a magnetic stir bar and a septum was added compound R (7923.91 mg, 38.46 mmol), DCM (256.4 mL) and trifluoroacetic anhydride (18.64 mL, 132 mmol) at 25° C. The solution changed color from yellow to nearly colorless and the reaction was stirred for 10 minutes at 25° C. After 15 minutes, LCMS showed complete reaction. The solution was diluted with water and then extracted with DCM (3×25 ml). The combined organic fractions were washed with NaHCO$_3$ (saturated aqueous solution), brine and dried over MgSO$_4$, filtered and concentrated. The residue was purified on silica gel (BIOTAGE ZIP 30 g cart, gradient: 0-50% EtOAc/hexanes). The desired fractions were combined and dried to afford the title compound as a white solid (49% over 3 steps). LCMS: RT=0.627 min, M+H=188.0, >98% at 215 nm and 254 nm.

Ethyl 5-amino-3-chloro-4-methylthieno[2,3-c]pyridazine-6-carboxylate (T)

In a 100 mL round-bottom flask fitted with a magnetic stir bar and a septum was added IPA (192.31 mL), compound S (7230.86 mg, 38.46 mmol) and ethyl mercaptoacetate (3473.43 uL, 38.84 mmol) at 25° C. To this solution was added potassium carbonate (10631.11 mg, 76.92 mmol). The reaction suspension was stirred at RT until complete by LCMS analysis. EtOAc (100 mL) was added and sat. NH$_4$Cl solution (100 mL) until pH=4. The reaction was extracted with EtOAc (3×50 mL) and the combined organic fractions were washed with brine, dried over MgSO$_4$, filtered and concentrated. The residue was purified on silica gel (BIOTAGE ZIP 45 g cart; gradient: 5-100% EtOAc/hexanes). The desired fractions were combined and dried to yield the title compound (52-68% yield). LCMS: RT=0.791 min, M+H=258.2, >98% at 215 nm and 254 nm.

Ethyl 5-bromo-3-chloro-4-methylthieno[2,3-c]pyridazine-6-carboxylate (U)

A solution of sodium nitrite (152 mg, 2.21 mmol) in water (2.5 mL) was added dropwise to a mixture of compound T (0.5 g, 1.84 mmol) and cupric bromide (373 mg, 1.66 mmol) in HBr (43 mL, 48 wt % in H$_2$O) at 0° C. After 1 hr at 0° C., additional HBr (3.0 mL, 48 wt % in H$_2$O) was added. After 16 hr at rt, the reaction was diluted with EtOAc (35 mL) and washed with saturated aqueous Na$_2$CO$_3$. The separated organic layer was dried over Na$_2$SO$_4$, filtered and concentrated. The residue was purified on silica gel (40 g, gradient: 0-40% EtOAc/hexanes) to afford the title compound (260 mg, 42% yield). ES-MS [M+1]$^+$: 337.0.

Ethyl (E)-3-chloro-5-(2-ethoxyvinyl)-4-methylthieno[2,3-c]pyridazine-6-carboxylate (V)

Compound U (0.26 g, 0.77 mmol, 1 eq.), (E)-1-ethoxyethene-2-boronic acid pinacol ester (0.23 g, 1.16 mmol, 1.5 eq.), Pd$_2$(dppf)$_2$Cl$_2$ (28 mg, 0.04 mmol, 0.05 eq.), cesium carbonate (0.76 g, 2.32 mmol, 3 eq.), water (0.8 mL) and 1,4-dioxane (3 mL) were added to a vial (20 mL). After bubbling nitrogen through the solution for 5 minutes, the vial was capped and heated to 90° C. for 2 hours. The reaction was filtered over a pad of Celite, washed with EtOAc (3×) and washed with H$_2$O and brine. After the organic layer was dried (Na$_2$SO$_4$), solvent was removed under vacuo to afford desired product. The material was taken through without further purification. ES-MS [M+1]$^+$: 327.3.

3-Chloro-4-methylpyrido[4',3':4,5]thieno[2,3-c]pyridazin-8-ol (W)

In a microwave vial, a solution of compound V (0.26 g, 0.80 mmol, 1.0 eq) in trifluoroacetic acid (3 mL) was heated in a Biotage microwave at 125° C. for 1 hr. The reaction was followed by LCMS and subjected to further microwave irradiation until reaction was complete. The solution was concentrated under vacuo and azeotroped with toluene (2×50 mL). The residue was combined in a reinforced pressure vessel with NH$_4$OH (10.5 mL) and the vessel was sealed and heated to 100° C. for 1 hr. The mixture was concentrated and then the residue was suspended in IPA (2 mL). After sonication, the solids were collected via filtration to afford desired product (158 mg, 79%). ES-MS [M+1]$^+$: 252.0.

3,8-Dichloro-4-methylpyrido[4',3':4,5]thieno[2,3-c]pyridazine (X)

Phosphorus oxychloride (0.5 mL) was added to a solution of compound W (10 mg, 0.04 mmol, 1 eq) in DCE (1.0 mL) and the mixture was subjected to microwave reactor at 120° C. for 30 minutes. The solution was concentrated and the residue suspended in DCM (10 mL) and sat. NaHCO$_3$ (aq). The organic layer was separated, dried (Na$_2$SO$_4$) and concentrated. The material was taken through to the next step without further purification. ES-MS [M+1]$^+$: 285.8

3-Chloro-N-(4-methoxybenzyl)-4-methylpyrido[4',3':4,5]thieno[2,3-c]pyridazin-8-amine (Compound 32)

Compound X (10 mg, 0.04 mmol, 1 eq.), 4-methoxybenzylamine (6 mg, 0.044 mmol, 1.1 eq.), DIEA (0.032 mL, 0.18 mmol, 5.0 eq.) and NMP (1 mL) were added to a microwave vial. The vial was capped and heated in a microwave reactor to 160° C. for 1 hour. The residue was purified by reverse phase HPLC (5-70% acetonitrile: water with 0.1% TFA). The desired fractions were collected and neutralized with a saturated solution of NaHCO$_3$. The mixture was extracted with CHCl$_3$/IPA (3:1, 3×). The collected organic layers were concentrated to afford 1.1 mg (6%) of the title compound. ES-MS [M+1]$^+$: 371.3; 1H NMR (400 MHz, CDCl$_3$): δ 8.25 (d, J=6.2 Hz, 1H), 7.61 (d, J=6.2 Hz, 1H), 7.40 (d, J=7.8 Hz, 2H), 6.94 (d, J=7.8 Hz, 2H), 4.91 (s, 2H), 3.86 (s, 3H), 3.05 (s, 3H).

The compounds shown in Table 4 were prepared in an analogous manner with the appropriate starting materials.

TABLE 4

| Cpd. No. | Name | Structure | ES-MS [M + 1]$^+$ |
|---|---|---|---|
| 33 | 3-chloro-4-methyl-N-(1-(5-(trifluoromethyl)pyrimidin-2-yl)azetidin-3-yl)pyrido[4',3':4,5]thieno[2,3-c]pyridazin-8-amine, 2,2,2-trifluoroacetic acid salt | 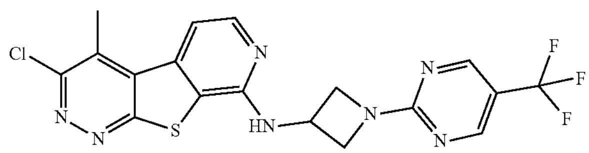 [SMILES: Cc1c(Cl)nnc2sc3c(NC4CN(c5ncc(C(F)(F)F)cn5)C4)nccc3c12] | 451.8 |
| 34 | 3-chloro-N-cyclobutyl-4-methylpyrido[4',3':4,5]thieno[2,3-c]pyridazin-8-amine | 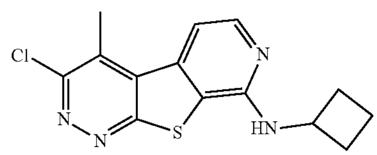 [SMILES: Cc1c(Cl)nnc2sc3c(NC4CCC4)nccc3c12] | 305.2 |
| 35 | 3-chloro-4-methyl-8-(pyrrolidin-1-yl)pyrido[4',3':4,5]thieno[2,3-c]pyridazine | 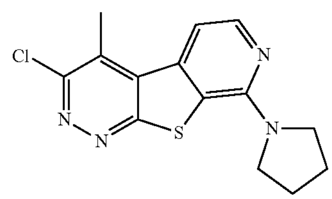 [SMILES: Cc1c(Cl)nnc2sc3c(N4CCCC4)nccc3c12] | 305.2 |
| 36 | 3-chloro-N-(3-fluoro-4-methoxybenzyl)-4-methylpyrido[4',3':4,5]thieno[2,3-c]pyridazin-8-amine | 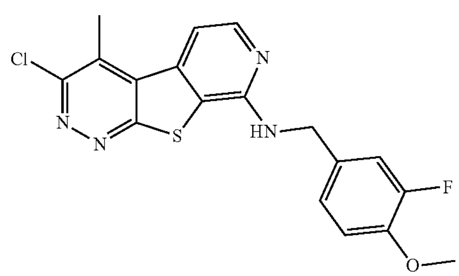 [SMILES: COc1ccc(CNc2nccc3c2sc2nnc(Cl)c(C)c23)cc1F] | 389.2 |

Example 7. 3-Methoxy-N-(4-methoxybenzyl)-4-methylpyrido[4',3':4,5]thieno[2,3-c]pyridazin-8-amine (Compound 37)

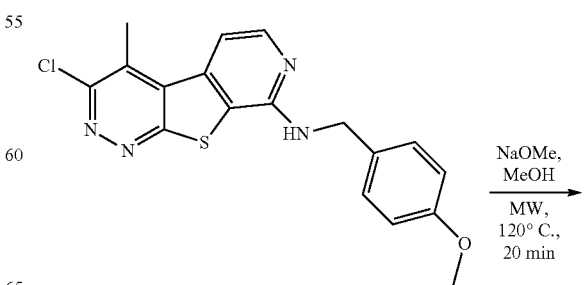

32

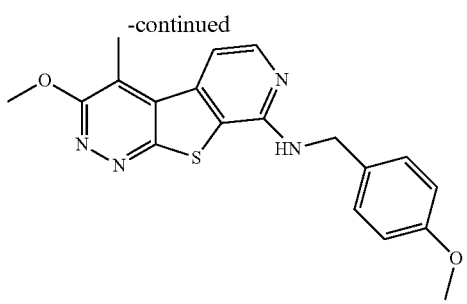

37

To a solution of Compound 32 (10 mg, 0.04 mmol, 1 eq.) in MeOH (1 mL) was added NaOMe (0.05 mL, 25 wt. % in methanol) in a microwave vial. The vial was capped and heated in a microwave reactor to 120° C. for 20 minutes. The solution was purified by reverse phase HPLC (0-90% acetonitrile: water with 0.05% NH$_4$OH) to afford 2.4 mg (15%) of the title compound. ES-MS [M+1]$^+$: 367.3; 1H NMR (400 MHz, CDCl$_3$): δ 8.35-8.28 (m, 1H), 7.56-7.48 (m, 1H), 7.44-7.35 (m, 2H), 7.00-6.90 (m, 2H), 4.80 (s, 2H), 4.63 (brs, 1H), 4.28 (s, 3H), 3.86 (s, 3H), 2.77 (s, 3H).

The compounds shown in Table 5 were prepared in an analogous manner with the appropriate starting materials.

TABLE 5

| Cpd. No. | Name | Structure | ES-MS [M + 1]$^+$ |
|---|---|---|---|
| 38 | 3-methoxy-4-methyl-N-(1-(5-(trifluoromethyl)pyrimidin-2-yl)azetidin-3-yl)pyrido[4',3':4,5]thieno[2,3-c]pyridazin-8-amine | 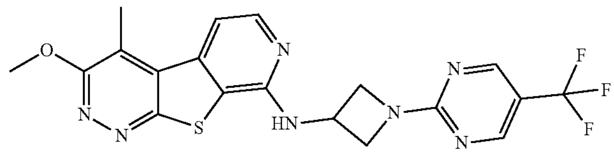 [SMILES: COc1nnc2sc3c(NC4CN(c5ncc(C(F)(F)F)cn5)C4)nccc3c2c1C] | 448.2 |
| 39 | N-cyclobutyl-3-methoxy-4-methylpyrido[4',3':4,5]thieno[2,3-c]pyridazin-8-amine | 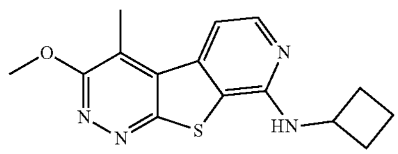 [SMILES: COc1nnc2sc3c(NC4CCC4)nccc3c2c1C] | 301.4 |

Example 8. 3-(Difluoromethyl)-4-methyl-8-(pyrrolidin-1-yl)pyrido[4',3':4,5]thieno[2,3-c]pyridazine (Compound 40)

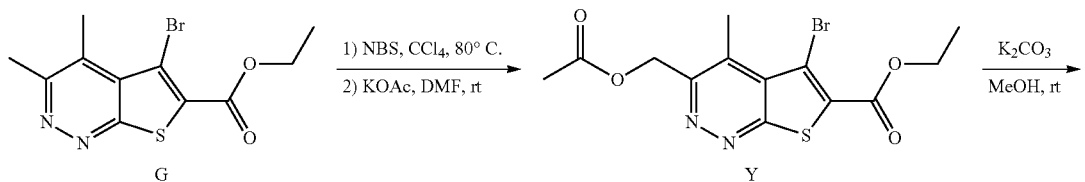

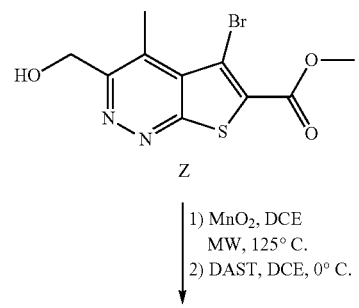

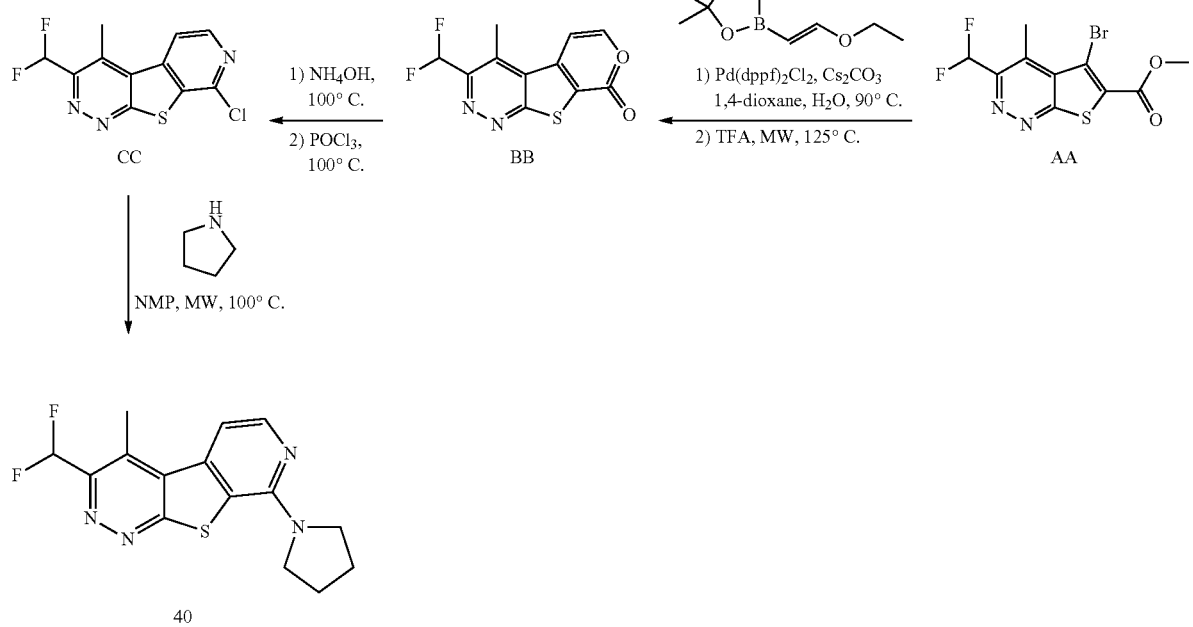

Ethyl 3-(acetoxymethyl)-5-bromo-4-methylthieno[2,3-c]pyridazine-6-carboxylate (Y)

Compound G (prepared as described in Example 3) (25 mg, 0.08 mmol) and N-bromosuccinimide (15.5 mg, 0.09 mmol) in carbon tetrachloride (0.5 mL) was stirred at 80° C. for 1 hr. The reaction was diluted with EtOAc, washed with sat. NaHCO$_3$ and brine, dried over Na$_2$SO$_4$ then concentrated. To the residue was added potassium acetate (12 mg, 0.12 mmol) and DMF (1 mL) and the mixture stirred at RT for 1 hr. The mixture was diluted with EtOAc, washed with H$_2$O (3×) and brine, dried over Na$_2$SO$_4$ then concentrated to give the title compound (21 mg, 70% yield) as a tan glass. ES-MS: 375.0 (M+2), 373.0 (M$^+$)

Methyl 5-bromo-3-hydroxymethyl-4-methylthieno[2,3-c]pyridazine-6-carboxylate (Z)

Compound Y (21 mg, 0.06 mmol) and potassium carbonate (22 mg, 0.16 mmol) in methanol (1 mL) were stirred at RT for 1 hr. The mixture was filtered and the filtrate concentrated to give the title compound (16 mg, 94% yield) as an amber glass. ES-MS: 319.2 (M+2), 317.2 (M$^+$).

Methyl 5-bromo-3-(difluoromethyl)-4-methyl-thieno[2,3-c]pyridazine-6-carboxylate (AA)

To compound Z (50 mg, 0.11 mmol) was added DCE (1.0 mL) and manganese dioxide (26 mg, 0.30 mmol) then the mixture was microwaved at 125° C. for 1 hr. The mixture was filtered and the filter cake washed with methanol/DCM (1:1.) The combined filtrates were concentrated to dryness then the residue was taken up in DCE (0.5 mL) and cooled to 0° C. (Diethylamino)sulfur trifluoride (72 mg, 0.44 mmol) was added and the solution stirred at 0° C. for 1 hr. The solution was diluted with EtOAc, washed with sat. NaHCO$_3$ and brine, dried over Na$_2$SO$_4$ then concentrated to give the title compound [32 mg, 60% yield] as a tan solid. ES-MS: 338.8 (M+2), 336.8 (M$^+$).

8-Chloro-3-(difluoromethyl)-4-methylpyrido[4',3':4,5]thieno[2,3-c]pyridazine (CC)

Compound AA (32 mg, 0.09 mmol), (E)-1-ethoxyethene-2-boronic acid pinacol ester (23 mg, 0.11 mmol) [1,1'-bis(diphenylphosphino)ferrocene]dichloropalladium (3 mg, 0.005 mmol) cesium carbonate (78 mg, 0.24 mmol) in 1,4-Dioxane (0.5 mL) and Water (0.1 mL) was stirred at 90° C. for 1 hr. The mixture was diluted with EtOAc, washed with H$_2$O and brine, dried over Na$_2$SO$_4$ then concentrated. To the residue was added trifluoroacetic acid (1 mL) and the mixture microwaved at 125° C. for 1 hr. The solution was concentrated to provide compound BB, which was used without further purification. To compound BB was added ammonium hydroxide (1.5 mL) was added and the mixture stirred at 100° C. for 1 hr. The mixture was concentrated then dried in vacuo. Phosphorus oxychloride (1.mL, 10.7 mmol) was added to the residue and the mixture stirred at 100° C. for 1 hr. The solution was concentrated and the residue dissolved in EtOAc, washed with sat. NaHCO$_3$ (aq) and brine, dried over Na$_2$SO$_4$ then concentrated to give the title compound (26 mg, 95% yield) as a dark brown solid. ES-MS [M+1]$^+$: 285.8.

3-(Difluoromethyl)-4-methyl-8-(pyrrolidin-1-yl)pyrido[4',3':4,5]thieno[2,3-c]pyridazine (Compound 40)

Compound CC (10 mg, 0.035 mmol) and pyrrolidine (25 mg, 0.35 mmol) in NMP (0.25 mL) was microwaved at 100° C. for 30 minutes. The solution was purified by semi-prep HPLC (5-60% MeCN in 0.1% NH$_4$OH (aq) over 8 minutes) to give Compound 40 (1.7 mg, 15% yield) as a tan glass. ES-MS [M+1]$^+$: 321.4.

The compounds shown in Table 6 were prepared in an analogous manner with the appropriate starting materials.

TABLE 6

| Cpd. No. | Name | Structure | ES-MS [M + 1]+ |
|---|---|---|---|
| 41 | 6-(3-(difluoromethyl)-4-methylpyrido[4',3':4,5]thieno[2,3-c]pyridazin-8-yl)-2-oxa-6-azaspiro[3.3]heptane | 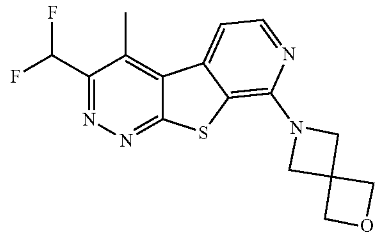 [SMILES: Cc1c(C(F)F)nnc2sc3c(N4CC5(COC5)C4)nccc3c12] | 349.4 |
| 42 | 3-(difluoromethyl)-4-methyl-8-(3-(pyridin-4-yl)azetidin-1-yl)pyrido[4'3':4,5]thieno[2,3-c]pyridazine | 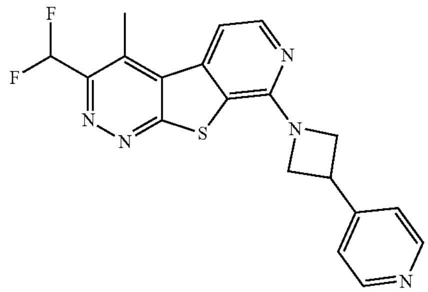 [SMILES: Cc1c(C(F)F)nnc2sc3c(N4CC(c5ccncc5)C4)nccc3c12] | 384.4 |

Example 9. Biological Activity

A. Cell Lines Expressing Muscarinic Acetylcholine Receptors

Human $M_4$ cDNA, along with the chimeric G protein $G_{qis}$, were transfected into Chinese hamster ovary (CHO-K1) cells purchased from the American Type Culture Collection using Lipofectamine2000. $M_4/G_{qi5}$/CHO cells were grown in Ham's F-12 medium containing 10% heat-inactivated fetal bovine serum (FBS), 20 mM HEPES, 500 μg/mL G418 sulfate, and 200 μg/mL Hygromycin B.

B. Cell-Based Functional Assay of Muscarinic Acetylcholine Receptor Activity For high throughput measurement of agonist-evoked increases in intracellular calcium, CHO-K1 cells stably expressing muscarinic receptors were plated in growth medium lacking G418 and hygromycin at 15,000 cells/20 μL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with assay buffer; the final volume was then aspirated to 20 μL. Next, 20 μL of a 2.3 μM stock of Fluo-4/acetoxymethyl ester (Invitrogen, Carlsbad, Calif.), prepared as a 2.3 mM stock in DMSO and mixed in a 1:1 ratio with 10% (w/v) Pluronic F-127 and diluted in assay buffer, was added to the wells and the cell plates were incubated for 50 minutes at 37° C. and 5% $CO_2$. Dye was removed by washing with the ELX 405 and the final volume was aspirated to 20 μL. Compound master plates were formatted in an 11 point concentration-response curve (CRC) format (1:3 dilutions) in 100% DMSO with a starting concentration of 10 mM using a BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 μL) to a 2× stock using a Thermo Fisher Combi (Thermo Fisher Scientific, Waltham, Mass.).

Calcium flux was measured using the Functional Drug Screening System (FDSS) 6000 or 7000 (Hamamatsu Corporation, Tokyo, Japan) as an increase in the fluorescent static ratio. Compounds were applied to cells (20 μL, 2×) using the automated system of the FDSS at 2-4 seconds into the protocol and the data were collected at 1 Hz. At approximately 144 seconds, L of an $EC_{20}$ concentration of the muscarinic receptor agonist acetylcholine was added (5×), followed by the addition of 12 μL of an $EC_{80}$ concentration of acetylcholine at approximately the 230 second time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. With the acetylcholine $EC_{20}$ set as baseline, the test compound $EC_{50}$ is determined as the concentration that produces an increase above baseline of 50% of the maximum increase in acetylcholine response elicited by the test compound. Antagonist activity was analyzed as a concentration-dependent decrease in the $EC_{80}$ acetylcholine response. Concentration-response curves were generated using a four-parameter logistical equation in XLFit curve fitting software (IDBS, Bridgewater, N.J.) for Excel (Microsoft, Redmond, Wash.) or Prism (GraphPad Software, Inc., San Diego, Calif.).

The above described assay was also operated in a second mode where an appropriate fixed concentration of the present compounds were added to the cells after establishment of a fluorescence baseline for about 3 seconds, and the response in cells was measured. 140 seconds later, the appropriate concentration of agonist was added and the calcium response (maximum-local minima response) was measured. The $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

C. Activity of Compounds in a mAChR $M_4$ Cell-Based Assay

Compounds were synthesized as described above. Activity ($EC_{50}$ and $E_{max}$) was determined in the mAChR $M_4$ cell-based functional assay as described above and the data are shown in Table 7. The compound number corresponds to the compound numbers used in Examples 2-8.

TABLE 7

| Cpd. No. | Human $M_4$ $EC_{50}$ (nM) | $E_{max}$ (%)* |
|---|---|---|
| 1 | 124 | 66.95 |
| 2 | 233 | 97.79 |
| 3 | 84.9 | 89.76 |
| 4 | 202 | 81.93 |
| 5 | 12.3 | 80.26 |
| 6 | 23.6 | 73 |
| 7 | 59.8 | 80.22 |
| 8 | 12.1 | 74.79 |
| 9 | 24.6 | 76.85 |
| 10 | 67.1 | 74.39 |
| 11 | 1030 | 72.83 |
| 12 | 18.2 | 77.41 |
| 13 | 66.0 | 81.88 |
| 14 | 14.3 | 91.33 |
| 15 | 34.3 | 97.41 |
| 16 | 194 | 81.46 |
| 17 | 1720 | 66.64 |
| 18 | 679 | 88.6 |
| 19 | 164 | 74.17 |
| 20 | 39.6 | 85.62 |
| 21 | 78.9 | 80.01 |
| 22 | 16.9 | 116.52 |
| 23 | 351 | 36.54 |
| 24 | 150 | 80.06 |
| 25 | >10 µM | 90.3 |
| 26 | 327 | 100.67 |
| 27 | 1100 | 102.03 |
| 28 | 4970 | 60.82 |
| 29 | 1540 | 72.94 |
| 30 | 714 | 79.46 |
| 31 | 2630 | 76.61 |
| 32 | 58.1 | 77.52 |
| 33 | 53.9 | 85.3 |
| 34 | 23.6 | 91.41 |
| 35 | 25.4 | 100.69 |
| 36 | 185 | 97.57 |
| 37 | 562 | 76.36 |
| 38 | 280 | 80.59 |
| 39 | 23.4 | 93.18 |
| 40 | 374 | 55.86 |
| 41 | 1880 | 54.83 |
| 42 | 442 | 56.15 |

*% ACh maximum at 30 µM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound of formula (I),

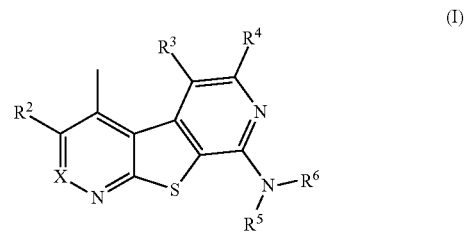

or a pharmaceutically acceptable salt thereof, wherein:
X is N or $CR^1$;
$R^1$, $R^2$, $R^3$ and $R^4$ are each independently selected from hydrogen, $C_1$-$C_4$-alkyl, $C_1$-$C_4$-haloalkyl, halo, and —$OR^a$;
—$NR^5R^6$ is selected from

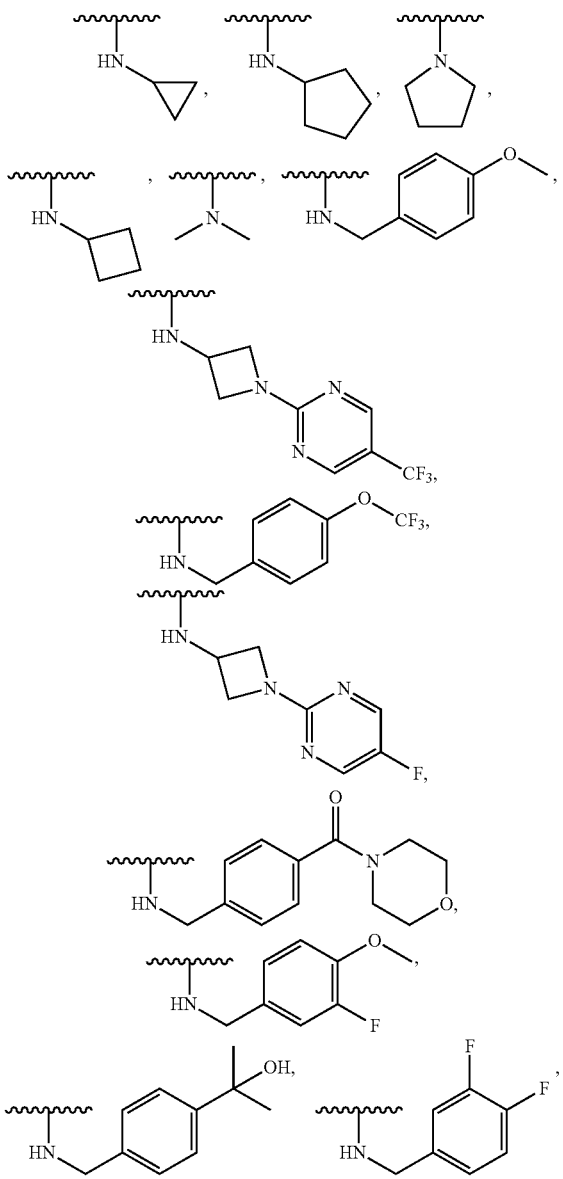

-continued

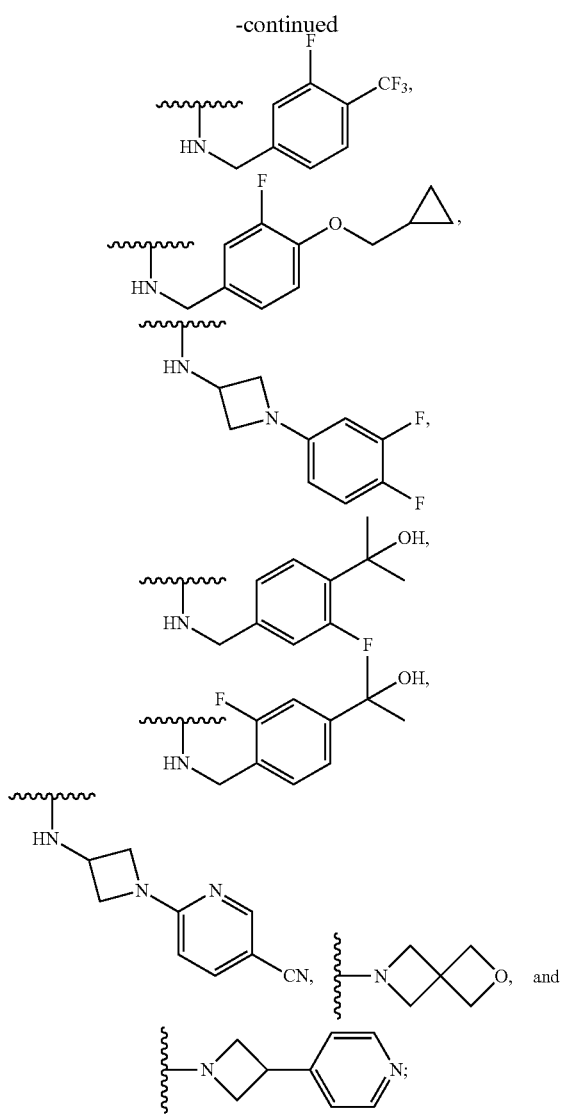

and
each $R^a$ is independently selected from hydrogen, $C_1$-$C_4$-alkyl, $C_1$-$C_4$-haloalkyl, aryl, heteroaryl, cycloalkyl, and heterocycle.

2. The compound of claim 1, wherein X is N.
3. The compound of claim 1, wherein X is $CR^1$.
4. The compound of claim 3, wherein $R^1$ is $C_1$-$C_4$ alkyl.
5. The compound of claim 4, wherein $R^1$ is methyl.
6. The compound of claim 1, wherein $R^2$ is hydrogen.
7. The compound of claim 1, wherein $R^2$ is $C_1$-$C_4$ alkyl.
8. The compound of claim 7, wherein $R^2$ is methyl.
9. The compound of claim 1, wherein $R^3$ is hydrogen.
10. The compound of claim 1, wherein $R^3$ is halo.

11. The compound of claim 1, wherein $R^3$ is chloro.
12. The compound of claim 1, wherein $R^4$ is hydrogen.
13. The compound of claim 1, wherein the compound is a compound of formula (Ia):

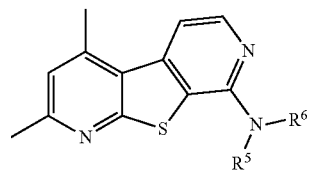

(Ia)

or a pharmaceutically acceptable salt thereof.

14. The compound of claim 1, wherein the compound is a compound of formula (Ib):

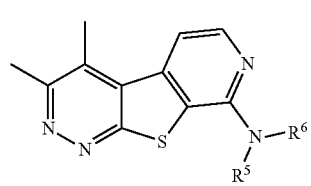

(Ib)

or a pharmaceutically acceptable salt thereof.

15. The compound of claim 1, wherein the compound is a compound of formula (Ic):

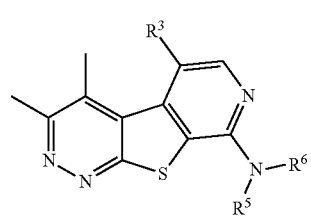

(Ic)

or a pharmaceutically acceptable salt thereof.

16. The compound of claim 1, wherein the compound is a compound of formula (Id):

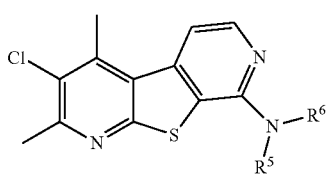

(Id)

or a pharmaceutically acceptable salt thereof.

17. The compound of claim 1, wherein the compound is a compound of formula (Ie):

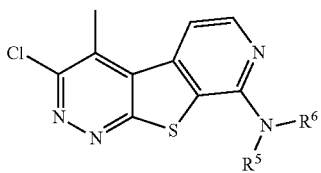

or a pharmaceutically acceptable salt thereof.

18. The compound of claim 1, wherein the compound is a compound of formula (f):

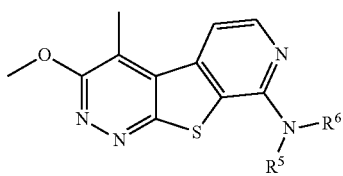

or a pharmaceutically acceptable salt thereof.

19. The compound of claim 1, wherein the compound is a compound of formula (Ig):

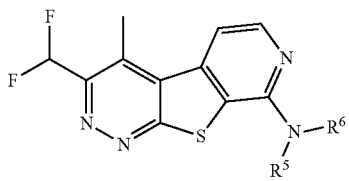

or a pharmaceutically acceptable salt thereof.

20. The compound of claim 1, selected from the group consisting of:
N-cyclopentyl-2,4-dimethylthieno[2,3-b:5,4-c']dipyridin-8-amine;
2,4-dimethyl-8-(pyrrolidin-1-yl)thieno[2,3-b:5,4-c']dipyridine;
N-cyclobutyl-2,4-dimethylthieno[2,3-b:5,4-c']dipyridin-8-amine;
N,N,2,4-tetramethylthieno[2,3-b:5,4-c']dipyridin-8-amine;
N-cyclopentyl-3,4-dimethyl-pyrido[4',3':4,5]thieno[2,3-c]pyridazin-8-amine;
3,4-dimethyl-8-pyrrolidin-1-yl-pyrido[4',3':4,5]thieno[2,3-c]pyridazine;
N-cyclobutyl-3,4-dimethyl-pyrido[4',3':4,5]thieno[2,3-c]pyridazin-8-amine;
N-cyclopropyl-3,4-dimethyl-pyrido[4',3':4,5]thieno[2,3-c]pyridazin-8-amine;
N-[(4-methoxyphenyl)methyl]-3,4-dimethyl-pyrido[4',3':4,5]thieno[2,3-c]pyridazin-8-amine;
3,4-dimethyl-N-[1-[5-(trifluoromethyl)pyrimidin-2-yl]azetidin-3-yl]pyrido[4',3':4,5]thieno[2,3-c]pyridazin-8-amine;
3,4-dimethyl-N-[[4-(trifluoromethoxy)phenyl]methyl]pyrido[4',3':4,5]thieno[2,3-c]pyridazin-8-amine;
N-[1-(5-fluoropyrimidin-2-yl)azetidin-3-yl]-3,4-dimethyl-pyrido[4',3':4,5]thieno[2,3-c]pyridazin-8-amine;
[4-[[(3,4-dimethylpyrido[4',3':4,5]thieno[2,3-c]pyridazin-8-yl)amino]methyl]phenyl]-morpholinomethanone;
N-[(3-fluoro-4-methoxy-phenyl)methyl]-3,4-dimethylpyrido[4',3':4,5]thieno[2,3-c]pyridazin-8-amine;
2-[4-[[(3,4-dimethylpyrido[4',3':4,5]thieno[2,3-c]pyridazin-8-yl)amino]methyl]phenyl]propan-2-ol;
N-[(3,4-difluorophenyl)methyl]-3,4-dimethyl-pyrido[4',3':4,5]thieno[2,3-c]pyridazin-8-amine;
N-[[3-fluoro-4-(trifluoromethyl)phenyl]methyl]-3,4-dimethyl-pyrido[4',3':4,5]thieno[2,3-c]pyridazin-8-amine;
N-[[4-(cyclopropylmethoxy)-3-fluoro-phenyl]methyl]-3,4-dimethyl-pyrido[4',3':4,5]thieno[2,3-c]pyridazin-8-amine;
N-[1-(3,4-difluorophenyl)azetidin-3-yl]-3,4-dimethyl-pyrido[4',3':4,5]thieno[2,3-c]pyridazin-8-amine;
2-[4-[[(3,4-dimethylpyrido[4',3':4,5]thieno[2,3-c]pyridazin-8-yl)amino]methyl]-2-fluoro-phenyl]propan-2-ol;
2-[4-[[(3,4-dimethylpyrido[4',3':4,5]thieno[2,3-c]pyridazin-8-yl)amino]methyl]-3-fluoro-phenyl]propan-2-ol;
6-[3-[(3,4-dimethylpyrido[4',3':4,5]thieno[2,3-c]pyridazin-8-yl)amino]azetidin-1-yl]pyridine-3-carbonitrile;
5-chloro-3,4-dimethyl-8-pyrrolidin-1-yl-pyrido[4',3':4,5]thieno[2,3-c]pyridazine;
2,4-dimethyl-N-(1-(5-(trifluoromethyl)pyrimidin-2-yl)azetidin-3-yl)thieno[2,3-b:5,4-c']dipyridin-8-amine;
N-(3-fluoro-4-methoxybenzyl)-2,4-dimethylthieno[2,3-b:5,4-c']dipyridin-8-amine;
2-(4-(((2,4-dimethylthieno[2,3-b:5,4-c']dipyridin-8-yl)amino)methyl)phenyl)propan-2-ol;
2-(4-(((2,4-dimethylthieno[2,3-b:5,4-c']dipyridin-8-yl)amino)methyl)-3-fluorophenyl)propan-2-ol;
3-chloro-N-(4-methoxybenzyl)-2,4-dimethylthieno[2,3-b:5,4-c']dipyridin-8-amine;
2-(4-(((3-chloro-2,4-dimethylthieno[2,3-b:5,4-c']dipyridin-8-yl)amino)methyl)phenyl)propan-2-ol;
3-chloro-2,4-dimethyl-8-(pyrrolidin-1-yl)thieno[2,3-b:5,4-c']dipyridine;
2-(4-(((3-chloro-2,4-dimethylthieno[2,3-b:5,4-c']dipyridin-8-yl)amino)methyl)-2-fluorophenyl)propan-2-ol;
3-chloro-N-(4-methoxybenzyl)-4-methylpyrido[4',3':4,5]thieno[2,3-c]pyridazin-8-amine;
3-chloro-4-methyl-N-(1-(5-(trifluoromethyl)pyrimidin-2-yl)azetidin-3-yl)pyrido[4',3':4,5]thieno[2,3-c]pyridazin-8-amine;
3-chloro-N-cyclobutyl-4-methylpyrido[4',3':4,5]thieno[2,3-c]pyridazin-8-amine;
3-chloro-4-methyl-8-(pyrrolidin-1-yl)pyrido[4',3':4,5]thieno[2,3-c]pyridazine;
3-chloro-N-(3-fluoro-4-methoxybenzyl)-4-methylpyrido[4',3':4,5]thieno[2,3-c]pyridazin-8-amine;
3-Methoxy-N-(4-methoxybenzyl)-4-methylpyrido[4',3':4,5]thieno[2,3-c]pyridazin-8-amine;
3-methoxy-4-methyl-N-(1-(5-(trifluoromethyl)pyrimidin-2-yl)azetidin-3-yl)pyrido[4',3':4,5]thieno[2,3-c]pyridazin-8-amine;
N-cyclobutyl-3-methoxy-4-methylpyrido[4',3':4,5]thieno[2,3-c]pyridazin-8-amine;
3-(difluoromethyl)-4-methyl-8-(pyrrolidin-1-yl)pyrido[4',3':4,5]thieno[2,3-c]pyridazine;
6-(3-(difluoromethyl)-4-methylpyrido[4',3':4,5]thieno[2,3-c]pyridazin-8-yl)-2-oxa-6-azaspiro[3.3]heptane; and
3-(difluoromethyl)-4-methyl-8-(3-(pyridin-4-yl)azetidin-1-yl)pyrido[4',3':4,5]thieno[2,3-c]pyridazine,
or a pharmaceutically acceptable salt thereof.

21. A pharmaceutical composition comprising a therapeutically effective amount of a compound of claim 1, or a pharmaceutically acceptable salt thereof, and a pharmaceutically acceptable carrier.

22. A method for treating a neurological and/or psychiatric disorder associated with muscarinic acetylcholine receptor dysfunction in a mammal, comprising a step of administering to the mammal a therapeutically effective amount a compound of claim 1, or pharmaceutically acceptable salt thereof.

23. The method of claim 22, wherein the disorder is selected from Alzheimer's disease, schizophrenia, a sleep disorder, a pain disorder, and a cognitive disorder.

24. The method of claim 22, wherein the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

25. A compound of formula (I),

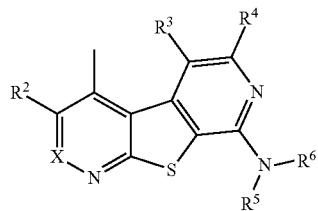

(I)

or a pharmaceutically acceptable salt thereof, wherein:
X is N or $CR^1$;
$R^1$, $R^2$, $R^3$ and $R^4$ are each independently selected from hydrogen, $C_1$-$C_4$-alkyl, $C_1$-$C_4$-haloalkyl, halo, and $-OR^a$;
each $R^a$ is independently selected from hydrogen, $C_1$-$C_4$-alkyl, $C_1$-$C_4$-haloalkyl, aryl, heteroaryl, cycloalkyl, and heterocycle;
$R^5$ is selected from hydrogen and methyl;
$R^6$ is selected from the group consisting of $C_1$-$C_4$ alkyl, $C_3$-$C_6$ cycloalkyl, a 3- to 6-membered heterocycle having one heteroatom selected from N and O, and $-(CR^bR^c)_n-Y$, wherein the cycloalkyl and the heterocycle are independently unsubstituted or substituted with 1 or 2 substituents independently selected from the group consisting of $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, halo, hydroxy, aryl, $C_3$-$C_6$ cycloalkyl, a 3- to 6-membered heterocycle having one heteroatom selected from N and O, and a 5- to 6-membered heteroaryl having 1 or 2 heteroatoms selected from N, O and S;
n is 1;
$R^b$ and $R^c$ are each hydrogen;
Y is phenyl, which is unsubstituted or substituted with 1 or 2 substituents independently selected from $C_1$-$C_4$ alkyl, $C_1$-$C_4$ haloalkyl, $C_1$-$C_4$ hydroxyalkyl, halo, hydroxy, —OR, and —COR; and
each R is independently selected from $C_3$-$C_6$-cycloalkyl-$C_1$-$C_4$-alkyl, and a 3- to 6-membered heterocycle having one or two heteroatoms selected from O, N, and S.

26. The compound of claim 25, or a pharmaceutically acceptable salt thereof, wherein:
$R^1$ is $C_1$-$C_4$ alkyl;
$R^2$ is hydrogen, $C_1$-$C_4$ alkyl, halo, $C_1$-$C_4$-haloalkyl, or $-OR^a$, wherein $R^a$ is $C_1$-$C_4$ alkyl;
$R^3$ is hydrogen or halo; and
$R^4$ is hydrogen.

27. A compound of formula (I),

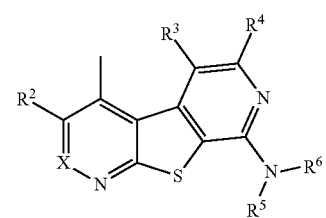

(I)

or a pharmaceutically acceptable salt thereof, wherein:
X is N or $CR^1$;
$R^1$, $R^2$, $R^3$ and $R^4$ are each independently selected from hydrogen, $C_1$-$C_4$-alkyl, $C_1$-$C_4$-haloalkyl, halo, and $-OR^a$;
each $R^a$ is independently selected from hydrogen, $C_1$-$C_4$-alkyl, $C_1$-$C_4$-haloalkyl, aryl, heteroaryl, cycloalkyl, and heterocycle; and
$R^5$ and $R^6$ are taken together with the nitrogen atom to which they are attached to form an azetidinyl, pyrrolidinyl, piperidinyl or piperazinyl group, wherein the azetidinyl is optionally substituted with a pyridinyl group.

28. The compound of claim 27, or a pharmaceutically acceptable salt thereof, wherein:
$R^1$ is $C_1$-$C_4$ alkyl;
$R^2$ is hydrogen, $C_1$-$C_4$ alkyl, halo, $C_1$-$C_4$-haloalkyl, or $-OR^a$, wherein $R^a$ is $C_1$-$C_4$ alkyl;
$R^3$ is hydrogen or halo; and
$R^4$ is hydrogen.

* * * * *